US009687417B2

(12) United States Patent
Demers et al.

(10) Patent No.: US 9,687,417 B2
(45) Date of Patent: Jun. 27, 2017

(54) COMPOUNDER APPARATUS

(71) Applicant: DEKA Products Limited Partnership, Manchester, NH (US)

(72) Inventors: Jason A. Demers, Manchester, NH (US); Frederick Morgan, Canton, MA (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 15/161,876

(22) Filed: May 23, 2016

(65) Prior Publication Data

US 2016/0262977 A1 Sep. 15, 2016

Related U.S. Application Data

(63) Continuation of application No. 14/656,945, filed on Mar. 13, 2015, now Pat. No. 9,364,394.

(Continued)

(51) Int. Cl.
*A61J 1/00* (2006.01)
*A61J 1/16* (2006.01)
(Continued)

(52) U.S. Cl.
CPC . *A61J 1/16* (2013.01); *A61J 1/20* (2013.01); *A61J 3/002* (2013.01); *B01F 13/1066* (2013.01)

(58) Field of Classification Search
CPC .................................. A61J 1/00; A61J 1/16
(Continued)

(56) References Cited

U.S. PATENT DOCUMENTS 6,050,400 A * 4/2000 Taskis .................. B65D 81/266
206/204
8,158,102 B2 4/2012 Demers et al.
(Continued)

FOREIGN PATENT DOCUMENTS

WO WO2013095459 A9 6/2013
WO WO2013096713 A2 6/2013
(Continued)

OTHER PUBLICATIONS

U.S. Appl. No. 62/341,396, filed May 25, 2016.
(Continued)

*Primary Examiner* — King M Chu
(74) *Attorney, Agent, or Firm* — James D. Wyninegar, Jr.

(57) ABSTRACT

A containment assembly for enclosing a medication container may comprise a first housing portion or interface portion having a proximal end and a distal end. The interface portion may include a housing wall which defines a channel spanning from the proximal end to the distal end. The channel may be open at the proximal and distal end. The containment assembly may further comprise at least one pierceable septum disposed at least at one of: on the proximal end of the channel and within the channel forming a barrier between the proximal end of the channel and distal end of the channel of the interface portion. The containment assembly may further comprise a variable-volume housing portion having a variable volume chamber. The variable-volume portion chamber of the variable-volume housing portion may be in fluid communication with the distal end of the channel.

20 Claims, 17 Drawing Sheets

Related U.S. Application Data

(60) Provisional application No. 61/953,036, filed on Mar. 14, 2014.

(51) Int. Cl.
*A61J 3/00* (2006.01)
*B01F 13/10* (2006.01)
*A61J 1/20* (2006.01)

(58) Field of Classification Search
USPC .................. 206/438, 53, 363, 366, 219, 220
See application file for complete search history.

(56) References Cited

U.S. PATENT DOCUMENTS

| | | |
|---|---|---|
| D728,779 S | 5/2015 | Sabin et al. |
| D735,319 S | 7/2015 | Sabin et al. |
| D736,370 S | 8/2015 | Sabin et al. |
| 9,151,646 B2 | 10/2015 | Kamen et al. |
| D745,661 S | 12/2015 | Collins et al. |
| D749,206 S | 2/2016 | Johnson et al. |
| D751,689 S | 3/2016 | Peret et al. |
| D751,690 S | 3/2016 | Peret et al. |
| D752,209 S | 3/2016 | Peret et al. |
| 9,295,778 B2 | 3/2016 | Kamen et al. |
| D754,065 S | 4/2016 | Gray et al. |
| D756,386 S | 5/2016 | Kendler et al. |
| D760,288 S | 6/2016 | Kendler et al. |
| D760,289 S | 6/2016 | Kendler et al. |
| 9,364,394 B2 | 6/2016 | Demers et al. |
| 9,372,486 B2 | 6/2016 | Peret et al. |
| D760,782 S | 7/2016 | Kendler et al. |
| D760,888 S | 7/2016 | Gill et al. |
| 9,400,873 B2 | 7/2016 | Kamen et al. |
| 2011/0313789 A1 | 12/2011 | Kamen et al. |
| 2012/0185267 A1 | 7/2012 | Kamen |
| 2013/0177455 A1 | 7/2013 | Kamen |
| 2013/0182381 A1 | 7/2013 | Gray |
| 2013/0184676 A1 | 7/2013 | Kamen |
| 2013/0188040 A1 | 7/2013 | Kamen |
| 2013/0191513 A1 | 7/2013 | Kamen |
| 2013/0197693 A1 | 8/2013 | Kamen |
| 2013/0204188 A1 | 8/2013 | Kamen |
| 2013/0272773 A1 | 10/2013 | Kamen |
| 2013/0281965 A1 | 10/2013 | Kamen |
| 2013/0297330 A1 | 11/2013 | Kamen |
| 2013/0310990 A1 | 11/2013 | Peret et al. |
| 2013/0317753 A1 | 11/2013 | Kamen |
| 2013/0317837 A1 | 11/2013 | Ballantyne |
| 2013/0336814 A1 | 12/2013 | Kamen |
| 2013/0339049 A1 | 12/2013 | Blumberg, Jr. |
| 2013/0346108 A1 | 12/2013 | Kamen |
| 2014/0165703 A1 | 6/2014 | Wilt |
| 2014/0180711 A1 | 6/2014 | Kamen |
| 2014/0188076 A1 | 7/2014 | Kamen |
| 2014/0188516 A1 | 7/2014 | Kamen |
| 2014/0195639 A1 | 7/2014 | Kamen |
| 2014/0227021 A1 | 8/2014 | Kamen |
| 2014/0318639 A1 | 10/2014 | Peret |
| 2014/0343492 A1 | 11/2014 | Kamen |
| 2015/0002667 A1 | 1/2015 | Peret et al. |
| 2015/0002668 A1 | 1/2015 | Peret et al. |
| 2015/0002677 A1 | 1/2015 | Peret et al. |
| 2015/0033823 A1 | 2/2015 | Blumberg, Jr. |
| 2015/0154364 A1 | 6/2015 | Biasi et al. |
| 2015/0157791 A1 | 6/2015 | Desch et al. |
| 2015/0238228 A1 | 8/2015 | Langenfeld et al. |
| 2015/0257974 A1 | 9/2015 | Demers et al. |
| 2015/0314083 A1 | 11/2015 | Blumberg, Jr. et al. |
| 2015/0332009 A1 | 11/2015 | Kane et al. |
| 2016/0055397 A1 | 2/2016 | Peret et al. |
| 2016/0055649 A1 | 2/2016 | Peret et al. |
| 2016/0061641 A1 | 3/2016 | Peret et al. |
| 2016/0063353 A1 | 3/2016 | Peret et al. |
| 2016/0073063 A1 | 3/2016 | Peret et al. |
| 2016/0084434 A1 | 3/2016 | Janway et al. |
| 2016/0097382 A1 | 4/2016 | Kamen et al. |
| 2016/0131272 A1 | 5/2016 | Yoo et al. |
| 2016/0158437 A1 | 6/2016 | Biasi et al. |
| 2016/0179086 A1 | 6/2016 | Peret et al. |
| 2016/0184510 A1 | 6/2016 | Kamen et al. |

FOREIGN PATENT DOCUMENTS

| | | |
|---|---|---|
| WO | WO2013096718 A2 | 6/2013 |
| WO | WO2013096722 A2 | 6/2013 |
| WO | WO2013096909 A2 | 6/2013 |
| WO | WO2013176770 A2 | 11/2013 |
| WO | WO2013177357 A1 | 11/2013 |
| WO | WO2014100557 A2 | 6/2014 |
| WO | WO2014100571 A2 | 6/2014 |
| WO | WO2014100658 A1 | 6/2014 |
| WO | WO2014100687 A2 | 6/2014 |
| WO | WO2014100736 A2 | 6/2014 |
| WO | WO2014100744 A2 | 6/2014 |
| WO | WO2014144557 A2 | 9/2014 |
| WO | PCT/US15/16796 | 2/2015 |
| WO | WO2015017275 A1 | 2/2015 |
| WO | PCT/US15/49952 | 9/2015 |
| WO | PCT/US2015/63359 | 12/2015 |

OTHER PUBLICATIONS

U.S. Appl. No. 29/569,450, filed Jun. 28, 2016.
U.S. Appl. No. 29/569,460, filed Jun. 28, 2016.
U.S. Appl. No. 15/205,538, filed Jul. 8, 2015.
U.S. Appl. No. 29/570,648, filed Jul. 11, 2016.
U.S. Appl. No. 61/297,544, filed Jan. 22, 2010.
U.S. Appl. No. 61/578,674, filed Dec. 21, 2011.
U.S. Appl. No. 61/578,649, filed Dec. 21, 2011.
U.S. Appl. No. 61/578,658, filed Dec. 21, 2011.
U.S. Appl. No. 61/651,322, filed May 24, 2012.
U.S. Appl. No. 61/679,117, filed Aug. 3, 2012.
U.S. Appl. No. 61/738,447, filed Dec. 18, 2012.
U.S. Appl. No. 61/740,474, filed Dec. 21, 2012.
U.S. Appl. No. 29/457,521, filed Jun. 11, 2013.
U.S. Appl. No. 61/843,574, filed Jul 8, 2013.
U.S. Appl. No. 61/860,398, filed Jul. 31, 2013.
U.S. Appl. No. 61/894,801, filed Oct. 23, 2013.
U.S. Appl. No. 61/900,431, filed Nov. 6, 2013.
U.S. Appl. No. 61/904,123, filed Nov. 14, 2013.
U.S. Appl. No. 29/477,236, filed Dec. 20, 2013.
U.S. Appl. No. 29/477,232, filed Dec. 20, 2013.
U.S. Appl. No. 29/477,231, filed Dec. 20, 2013.
U.S. Appl. No. 29/477,237, filed Dec. 20, 2013.
U.S. Appl. No. 29/477,249, filed Dec. 20, 2013.
U.S. Appl. No. 61/942,986, filed Feb. 21, 2014.
U.S. Appl. No. 61/953,036, filed Mar. 14, 2014.
U.S. Appl. No. 61/987,742, filed May 2, 2014.
U.S. Appl. No. 61/990,330, filed May 8, 2014.
U.S. Appl. No. 62/052,008, filed Sep. 18, 2014.
U.S. Appl. No. 62/086,356, filed Dec. 2, 2014.
U.S. Appl. No. 29/517,099, filed Feb. 10, 2015.
U.S. Appl. No. 29/517,095, filed Feb. 10, 2015.
U.S. Appl. No. 29/517,096, filed Feb. 10, 2015.
U.S. Appl. No. 29/517,100, filed Feb. 10, 2015.
U.S. Appl. No. 29/517,101, filed Feb. 10, 2015.
U.S. Appl. No. 29/517,097, filed Feb. 10, 2015.
U.S. Appl. No. 62/168,343, filed May 29, 2015.
U.S. Appl. No. 29/531,366, filed Jun. 25, 2015.
U.S. Appl. No. 29/532,660, filed Jul. 9, 2015.
U.S. Appl. No. 29/538,153, filed Sep. 1, 2015.
U.S. Appl. No. 62/212,871, filed Sep. 1, 2015.
U.S. Appl. No. 14/853,300, filed Sep. 14, 2015.
U.S. Appl. No. 14/939,586, filed Nov. 12, 2015.
U.S. Appl. No. 29/547,405, filed Dec. 3, 2015.
U.S. Appl. No. 29/547,402, filed Dec. 3, 2015.
U.S. Appl. No. 29/548,225, filed Dec. 11, 2015.
U.S. Appl. No. 29/552,303, filed Jan. 21, 2016.

(56) References Cited

OTHER PUBLICATIONS

U.S. Appl. No. 29/552,943, filed Jan. 27, 2016.
U.S. Appl. No. 29/552,942, filed Jan. 27, 2016.
U.S. Appl. No. 29/553,094, filed Jan. 28, 2016.
U.S. Appl. No. 62/288,132, filed Jan. 28, 2016.
U.S. Appl. No. 29/556,048, filed Feb. 26, 2016.
U.S. Appl. No. 15/055,941, filed Feb. 29, 2016.
U.S. Appl. No. 15/059,394, filed Mar. 3, 2016.
U.S. Appl. No. 15/077,389, filed Mar. 22, 2016.
U.S. Appl. No. 29/561,572, filed Apr. 18, 2016.
U.S. Appl. No. 29/564,750, filed May 16, 2016.
U.S. Appl. No. 15/163,906, filed May 25, 2016.
U.S. Appl. No. 29/565,908, filed May 25, 2016.

* cited by examiner

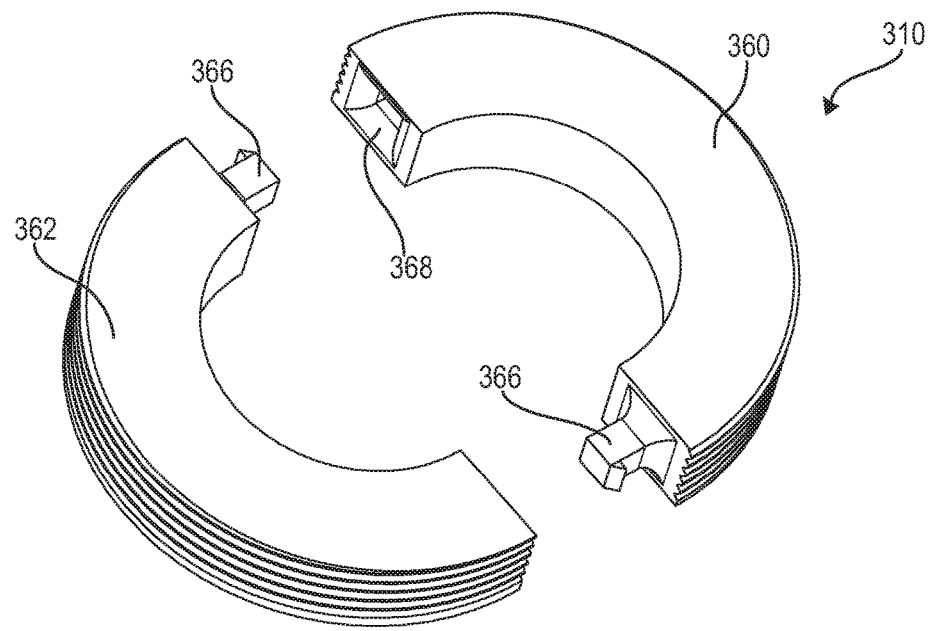
FIG. 13
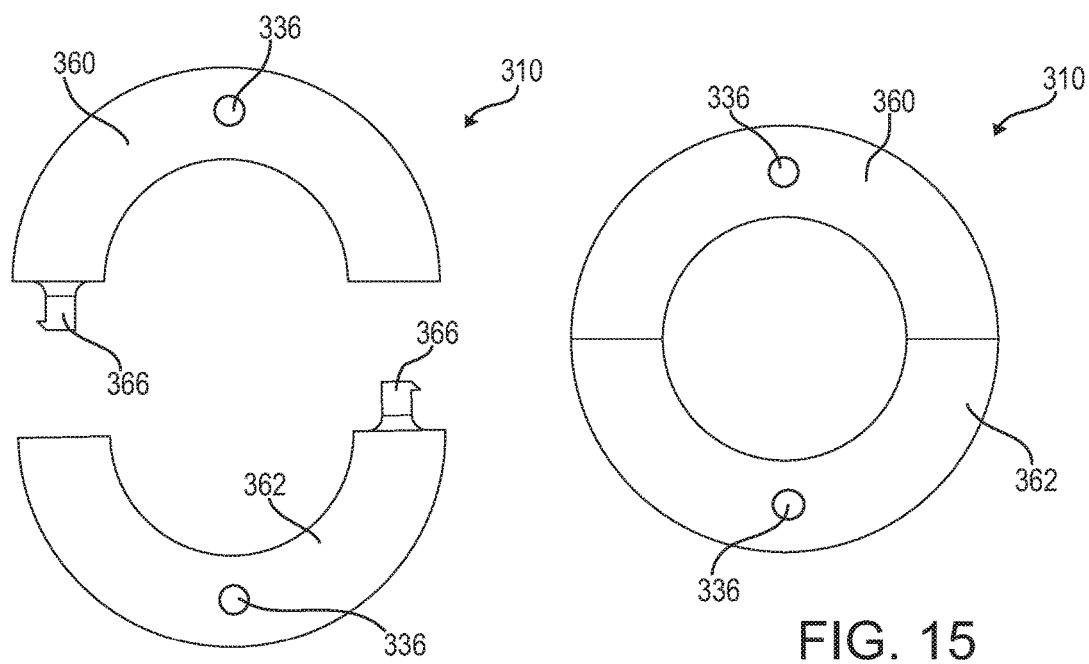
FIG. 14
FIG. 15

COMPOUNDER APPARATUS

CROSS REFERENCE TO RELATED APPLICATIONS

This application is a continuation application of U.S. Ser. No. 14/656,945, entitled "Compounder Apparatus", filed on Mar. 13, 2015, which claims the benefit of U.S. Provisional Application Ser. No. 61/953,036 filed Mar. 14, 2014 and entitled Compounder Apparatus, each of which is hereby incorporated herein by reference in its entirety.

BACKGROUND

Field of Disclosure

The present disclosure relates to the creation of multi-ingredient mixtures. More specifically, the present disclosure relates to the compounding of material, such as medications.

Description of Related Art

In many fields and for many applications, it is important to create a mixture from a combination of multiple ingredients. To achieve a desired end result, it is important that these ingredients are mixed with a degree of precision to ensure that each ingredient is present in a proper concentration when finished. Manual mixing of ingredients may be performed; however, this may be inefficient, imprecise, error prone, and time consuming among other draw backs. Additionally, some ingredients may be unsafe, or otherwise hazardous to mix by hand. It may, therefore, be desirable that an automated mixing apparatus be used.

SUMMARY

A compounder apparatus may include a manifold. A number of reservoirs may be docked to the manifold. The compounder apparatus may include a means of extracting fluid from the reservoirs. The compounder apparatus may include a means of mixing the extracted fluid with a diluent. The compounder apparatus may include a mixing chamber for compounding pharmaceuticals. The compounder apparatus may fill a destination reservoir in communication with the compounder with the compounded pharmaceutical.

In accordance with an embodiment of the present disclosure, a containment assembly for enclosing a medication vial may comprise a first housing portion or interface portion having a proximal end and a distal end. The interface portion may include a housing wall which defines a channel spanning from the proximal end to the distal end. The channel may be open at the proximal and distal end. The containment assembly may further comprise at least one pierceable septum disposed at least at one of: on the proximal end of the channel and within the channel forming a barrier between the proximal end of the channel and distal end of the channel of the interface portion. The containment assembly may further comprise a variable-volume housing portion having a variable volume chamber. The variable-volume portion chamber of the variable-volume housing portion may be in fluid communication with the distal end of the channel.

In some embodiments the distal end of the interface portion may include a mating feature which mates with a cooperating mating feature of the variable-volume housing portion. In some embodiments the containment assembly may further comprise a gasket member configured to compress between the interface portion and the variable-volume housing portion when the interface portion is mated to the variable-volume housing portion. In some embodiments the containment assembly may further comprise an adapter member having a mating feature configured to mate with a cooperating mating feature on one of the interface portion and the variable-volume housing portion. In some embodiments, the adapter may be a collar which is adapted to fit around a portion of the medication vial. In some embodiments, the adapter may be a collar which is adapted to fit around the neck of a medication vial. In some embodiments, the adapter may include at least one pass-through allowing for fluid communication between the distal end of the channel and the variable-volume portion chamber. In some embodiments, the containment assembly may further comprise at least two pierceable septa disposed within the channel. A first septum of the at least two septa may be disposed proximal the proximal end. A second septum of the at least two septa may be disposed distal the proximal end relative to the first septum. In some embodiments, the variable-volume portion chamber may be formed from an elastomeric material. In some embodiments, the variable-volume portion chamber may include at least one expandable feature. In some embodiments, the at least one expandable feature may be a collapsible pleat. In some embodiments, the variable-volume housing portion may include a window.

In accordance with another embodiment of the present disclosure, a containment assembly for enclosing a medication vial may comprise an interface portion having a proximal end and a distal end. The interface portion may include a housing wall which defines a channel spanning from the proximal end to the distal end. The channel may be open at the proximal and distal end. The containment assembly may further comprise a plurality of elastomeric septa disposed within the channel forming a barrier between the proximal end of the channel and distal end of the channel. The containment assembly may further comprise a variable-volume housing portion. At least a portion of the variable-volume housing portion may be of variable volume and formed of an elastomeric material.

In some embodiments, the variable-volume portion chamber of the variable-volume housing portion may be in fluid communication with the distal end of the channel. In some embodiments, the second housing portion may include a pressure port configured for connection to a pressure source. The pressure port may be a vacuum port and the pressure source may be a vacuum source. In some embodiments, the variable volume may be a flaccid enclosure. In some embodiments, the containment assembly may further comprise a collar member which couples with one of the interface portion or variable-volume housing portion. The collar member may be sized to fit around the neck of the medication vial. In some embodiments, the collar member may include a passage which allows for fluid communication between the distal end of the channel and the variable volume. In some embodiments, the collar member may comprise a first part and a second part. The first and second part may have cooperating coupling features which engage to couple the first part and second part together.

BRIEF DESCRIPTION OF THE DRAWINGS

These and other aspects will become more apparent from the following detailed description of the various embodiments of the present disclosure with reference to the drawings wherein:

FIGS. 13-15 depict various view of an example adapter for a drug reservoir containment assembly;

DETAILED DESCRIPTION

Figure 1:
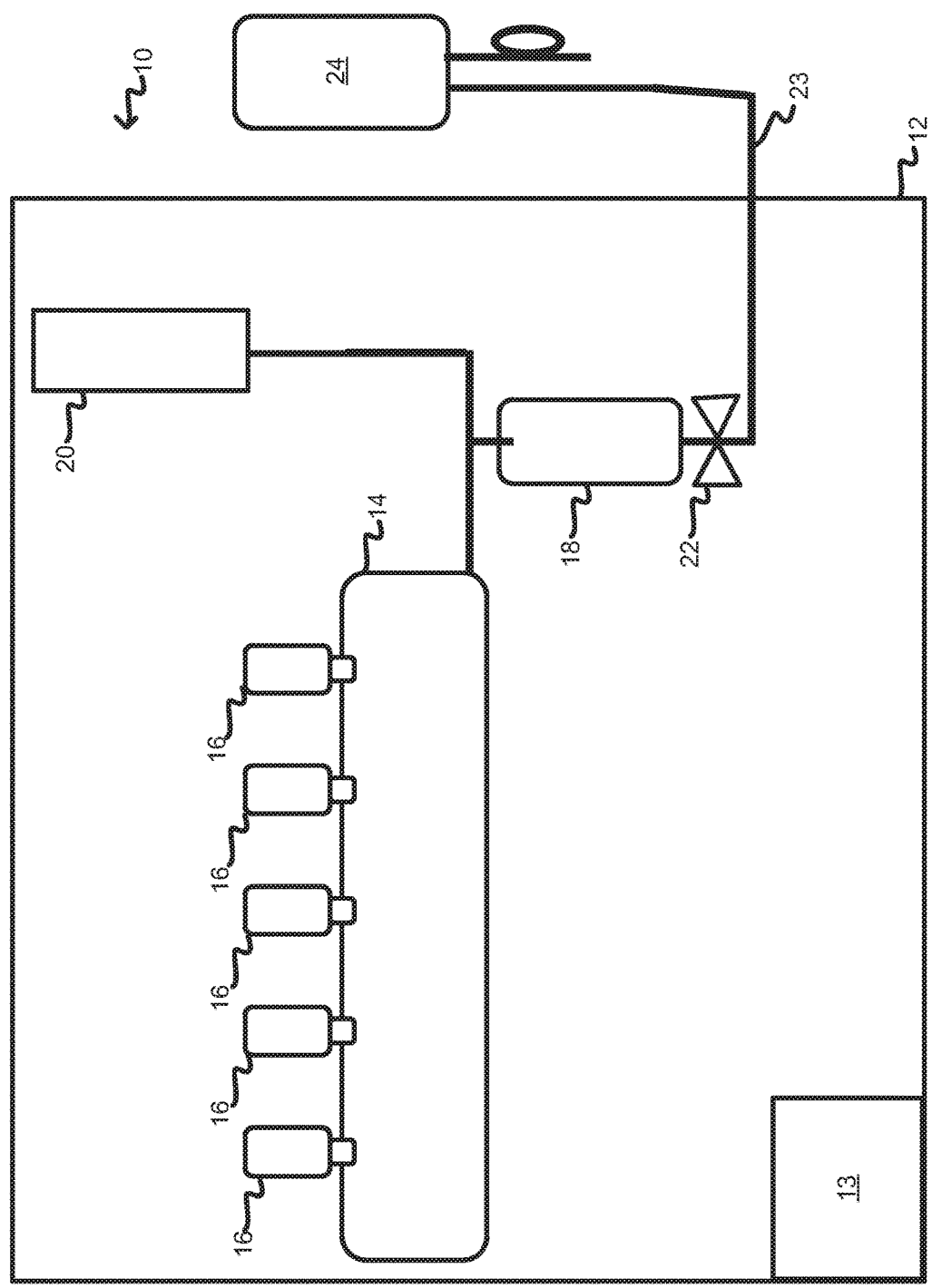
FIG. 1 depicts a first example representative block diagram of a compounder.

FIG. 1 depicts an example representative block diagram of a compounder apparatus 10 (sometimes referred to herein simply as compounder 10 or apparatus 10) in accordance with an embodiment of the present disclosure. In specific embodiments, the compounder 10 may be adapted for use to precisely mix a number of products and solutions. Various examples may include, but are not limited to: soda, coffee, adult beverages, chemicals, paint, parenteral nutrition formulations, pharmaceuticals, fillers, solvents, gases, etc. The example compounder 10 depicted in FIG. 1 is shown as a pharmaceutical compounder. Such a compounder 10 may be used to prepare medications for any number of applications. In some embodiments, the compounder 10 may be used to prepare one or more of the following: chemotherapy drugs, epidurals, dialysis solution, cardioplegia drugs, etc. for later administration to a patient. Alternatively, in some embodiments, the compounder 10 may be part of a bedside system which delivers fluid directly to a patient or to an apparatus that will deliver the fluid to the patient.

The compounder 10 may include a housing 12. The housing 12 may enclose various reservoirs, fluid pathways, valves, manifolds, chambers, control circuitry, sensors, etc. that are included as parts of the compounder 10. The housing 12 may be any suitable enclosure constructed of any suitable material or combination of suitable materials. In various embodiments, the interior volume of the housing 12 may be a controlled environment, or may be divided into a number of controlled environments. In such embodiments, the controlled portion(s) of the housing 12 may be sealed, insulated, etc. to facilitate control of that portion of the housing 12.

In some embodiments, the interior volume or a portion of the interior volume of the housing 12 may be controlled to be relatively free of particulates and/or contaminates or meet a desired cleanroom standard. In such embodiments, the compounder 10 may include various filters (not shown) and circulation fans (not shown). Additionally, the interior volume of the housing 12 may be positively pressurized to help ensure air from an uncontrolled environment may not ingress into the housing 12 in the event that there is a leak. The interior volume, or a portion of the interior volume of the housing 12 may be temperature controlled. In such embodiments, the compounder 10 may include thermal control components (not shown) such as a heater and/or refrigeration system, temperature sensors, etc. In some embodiments, the interior volume of the housing 12 may be controlled based on humidity, light levels or wavelengths, etc. and include such components as necessary to accomplish such control.

The compounder 10 may include a user interface 13. The user interface 13 may be a graphic user interface such as a touch screen or any other suitable user interface. The user interface 13 may be used by a user to control operation of or program the compounder 10, check status of the compounder 10, convey status messages from the compounder 10, provide troubleshooting or help screens to a user, etc.

In the example embodiment, the user interface 13 is shown as a part of the compounder 10, however, this need not be so in all embodiments. In some embodiments, the user interface 13 may be external to the compounder 10. For example, the user interface 13 may be accessed through a tablet, PC, smart phone, or any other suitable platform.

As shown, the compounder 10 includes a manifold 14. A number of reservoirs 16 are docked on the manifold 14. In the example embodiment, five reservoirs may be docked on the manifold 14. In other embodiments, the manifold 14 may be adapted such that any suitable number of reservoirs 16 may be docked on a manifold 14. This may be desirable in order to make a compounder 10 more versatile and able to concoct a larger number of compounded medications or other mixtures. Some embodiments may include more than one manifold 14. For example, there may be a number of manifolds 14 arranged in parallel. This may also help to increase the range of compounded medications or mixtures which the compounder 10 may create. Additionally, having multiple manifolds 14 may help to increase the overall throughput of a compounder 10. In some specific embodiments, the manifold(s) 14 may be configured to dock at least 63 reservoirs 16.

A manifold 14 for the compounder 10 may be constructed in any suitable manner. In some embodiments, the manifold 14 may be machined, injection molded, or generated with an additive manufacturing process such as selective laser sintering, etc. It may also be desirable that a manifold 14 for the compounder 10 be of a material which will not be compromised by repeated sterilization. For example, it may be desirable that a manifold 14 be made from high temperature, heat resistant plastic.

The reservoirs 16, in the example embodiment, may be medication vials. In other embodiments, the reservoirs 16 may not be medication vials. In applications where the compounder 10 is adapted for use in beverage mixing the reservoirs 16 may contain drink concentrates, liquors, drink additives, etc. In applications where the compounder 10 is adapted for use in paint mixing, the reservoirs may be various colors of paint. In other embodiments, the reservoirs 16 may contain other fluids, solutions, materials, etc.

Fluid may be selectively extracted from the reservoirs 16 and into the manifold 14. This may be done in any suitable fashion. In some embodiments, a positive pressure may be created in the reservoir 16 such that fluid is forced out of the reservoir 16. In some embodiments, a vacuum or partial vacuum may be drawn downstream of the reservoir 16 to suck fluid out of the reservoir 16. In some embodiments, a reservoir 16 may be elastomeric and may exert a force on the fluid contained within the reservoir 16 that squeezes the contained fluid out of the reservoir 16. In some embodiments, a reservoir 16 may be flaccid or flexible and be surrounded by an inflatable bladder or pressurizable chamber. As the bladder is inflated or the pressurizable chamber is pressurized, the flaccid reservoir 16 may be forced to collapse and fluid may be forced out of the reservoir 16.

The manifold 14 may include various valves to facilitate extraction of fluid from the reservoirs 16 in a controlled manner. For example, a valve may be positioned downstream of a reservoir dock on a manifold 14. As pressure is exerted on the fluid in a reservoir 16 on that dock or port, the valve may be opened and closed to allow a desired amount of fluid to escape from the reservoir 16. Each time the valve is opened and closed the volume of fluid which escapes from the reservoir 16 may be measured. The valve may be cycled open and closed until the proper amount of fluid has left the reservoir 16

Fluid from the reservoir 16 may be routed through the various fluid passageways of the manifold 14 and into a mixing chamber 18. Additionally, the mixing chamber 18 may be selectively put into communication with a diluent source 20. In the mixing chamber 18, diluent from the diluent source 20 may be added to the fluid from the reservoirs 16 to dilute the reservoir 16 fluids to a lower concentration. In some embodiments, multiple diluent sources 20 may be included. This may be desirable since different medications may need to be diluted with different diluents. In some embodiments, the mixing chamber 18 may be actively agitated or otherwise controlled in a manner that would facilitate mixing of fluid in the mixing chamber 18.

A valve 22 may be actuated to allow fluid to flow from the mixing chamber 18 to a fluid line 23 and into a destination reservoir 24. The destination reservoir 24 may be any type of suitable reservoir for a compounded medication or mixture. In the example embodiment, the destination reservoir 24 is shown as an IV bag. Other types of medication reservoirs may also be used as the destination reservoir 24. For example, a medication vial, syringe, bladder, cassette, or any other drug containing volume or vessel may be used as a destination reservoir 24. In some embodiments, a patient may be the reservoir 24.

In embodiments where the compounder 10 is not a pharmaceutical compounder, the destination reservoir 24 may differ. For example, if the compounder 10 is for use in the mixing of beverages, the destination reservoir 24 may be a cup, glass, bottle, can, mug, thermos, or the like. In embodiments where the compounder 10 is for use in the mixing of paints, the destination reservoir 24 may be a paint can or the like.

Figure 2:
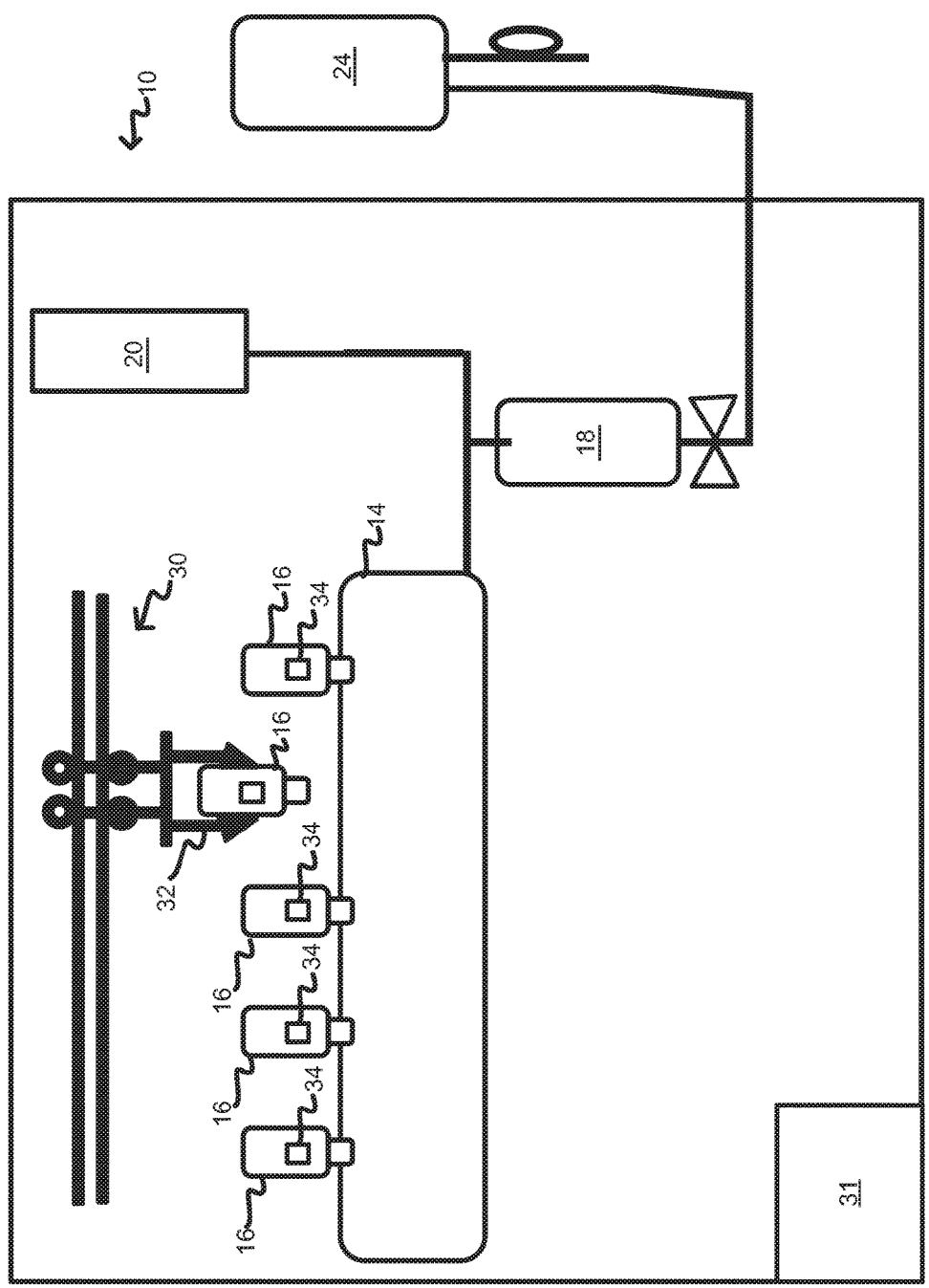
FIG. 2 depicts a second example representative block diagram of a compounder.

FIG. 2 depicts another example embodiment of a compounder 10. The compounder 10 shown in FIG. 2 includes a gantry 30. The gantry 30 may be used move reservoirs 16 onto and off of a manifold 14. In other embodiments, any other means of moving reservoirs 16 onto and off of the manifold 14 may be used. For example, a mechanized armature or the like may be used.

The gantry 30 may be controlled by a controller 31 The controller 31 may command movement of a crane 32 of the gantry 30 using, for example, an x,y coordinate system. As shown in FIG. 2, a reservoir 16 is held by the crane of the gantry 30. The crane 32 of the gantry 30 has been maneuvered over an open port of the manifold 14 in FIG. 2. This may be accomplished by the controller 31 commanding the crane 32 of the gantry 30 to move to the specific coordinate of the open port on the manifold 14. The controller 31 may then lower crane 32 to place the reservoir 16 on the manifold 14. The manifold 14 may include a retaining feature or the like to ensure that the reservoir 16 is securely held on the manifold 14. Additionally, in some embodiments, the interface between the reservoir 16 and the manifold 14 may be made to be fluid tight in some embodiments.

In some embodiments, the controller 31 may cause a unique identifier 34 on a reservoir 16 to be read before moving the reservoir 16 to an open port on a manifold 14. The unique identifier 34 may be any variety of unique identifier 34 and may identify the contents of the reservoir 16. The unique identifier 34 may be a barcode, RFID, magnetic strip, other smart identification, etc. There may, for example, be a unique identifier 34 for each drug (and each form and concentration of each drug if it comes in multiple forms/concentrations) which may be used in the compounder 10.

Based on the unique identifier 34, the controller 31 may identify a number of compatible ports on the manifold (s) 14. The controller 31 may then command the gantry 30 to move to a selected port of the compatible ports. For a compounder 10 used in the compounding of pharmaceuticals, compatible ports may, for example, be ports on manifolds 14 which do not include a contraindicated drug or ports on manifolds 14 made from compatible materials. In some embodiments, instead of identifying a number of compatible ports for a unique identifier 34, each unique identifier 34 may have an assigned manifold 14 port. Ports may be chosen for each unique identifier 34 in a manner which maximizes throughput, efficiency, and/or safety of the compounder 10.

In some embodiments, a user may instead or additionally manually identify the contents of the reservoir 16 on a user interface of the compounder 10. In embodiments where this is done in addition to the reading of a unique identifier 34 on the reservoir 16, the compounder 10 may generate an error if the contents of the reservoir 16 manually input by a user do not match the contents of the reservoir 16 as indicated by the unique identifier 34. Additionally, a user may identify which manifold 14 port they would like the reservoir 16 to be docked to in some embodiments. In such embodiments, if the port selected is incompatible (e.g. is on a manifold 14 with a contraindicated medication) with the contents of the reservoir 16 the compounder 10 may generate an error and not allow docking.

To remove a spent reservoir 16 from the manifold 14, the controller 31 may move the crane 32 of the gantry 30 to the location of the port of the manifold 14 where the spent reservoir 16 is docked. The crane 32 may then be lowered to the reservoir 16, pick up the reservoir 16 and remove the reservoir 16 from the manifold 14.

As mentioned above, in some embodiments, the manifold 14 may include a retaining feature which ensures that the reservoir 16 is securely retained on the manifold 14. In such embodiments, the crane 32 may include an unlocking feature which must engage with a portion of the manifold 14 for the reservoir 16 to be released from the retaining feature. When the crane 32 is lowered to the desired port on the manifold 14 correctly, the unlocking feature may operatively engage a portion of the manifold 14 such that the retaining feature may release the reservoir 16. Likewise, in some embodiments, a reservoir 16 may not be placed on the manifold 14 without the unlocking feature of the crane 32 engaging the appropriate portion of the manifold 14. In such embodiments, the retaining feature may also act as a receiving feature which precludes docking of a reservoir 16 on the manifold 14 unless the unlocking feature is properly engaged with the manifold 14.

In some embodiments, when a spent reservoir 16 is removed from a manifold 14 port, a controller 31 may command the gantry 30 to move to the coordinates of a bin or container (not shown) within the compounder 10. Such a bin or container may be used to store spent reservoirs 16. The bin or container may be removable once full. In some embodiments, the bin or container may seal once removed from the compounder 10. Once removed the bin or container may be replaced with a new bin or container.

In some embodiments, after removing a spent reservoir 16 the controller 31 may command the gantry 30 to retrieve a cover member for the manifold 14 port. The crane 32 may then place the cover member over the manifold 14 port. Alternatively, the controller 31 may command the gantry 30 to retrieve a cleaning or sterilizing cartridge which may then be placed over the port and used for cleaning or sterilization of the port.

Instead of moving randomly about a manifold 14 or number of manifolds 14, it may be desirable that the gantry 30 be controlled to work on manifold 14 ports which are in close spatial proximity to one another when possible. This may help to increase efficiency and throughput of the compounder 10.

Figure 3:
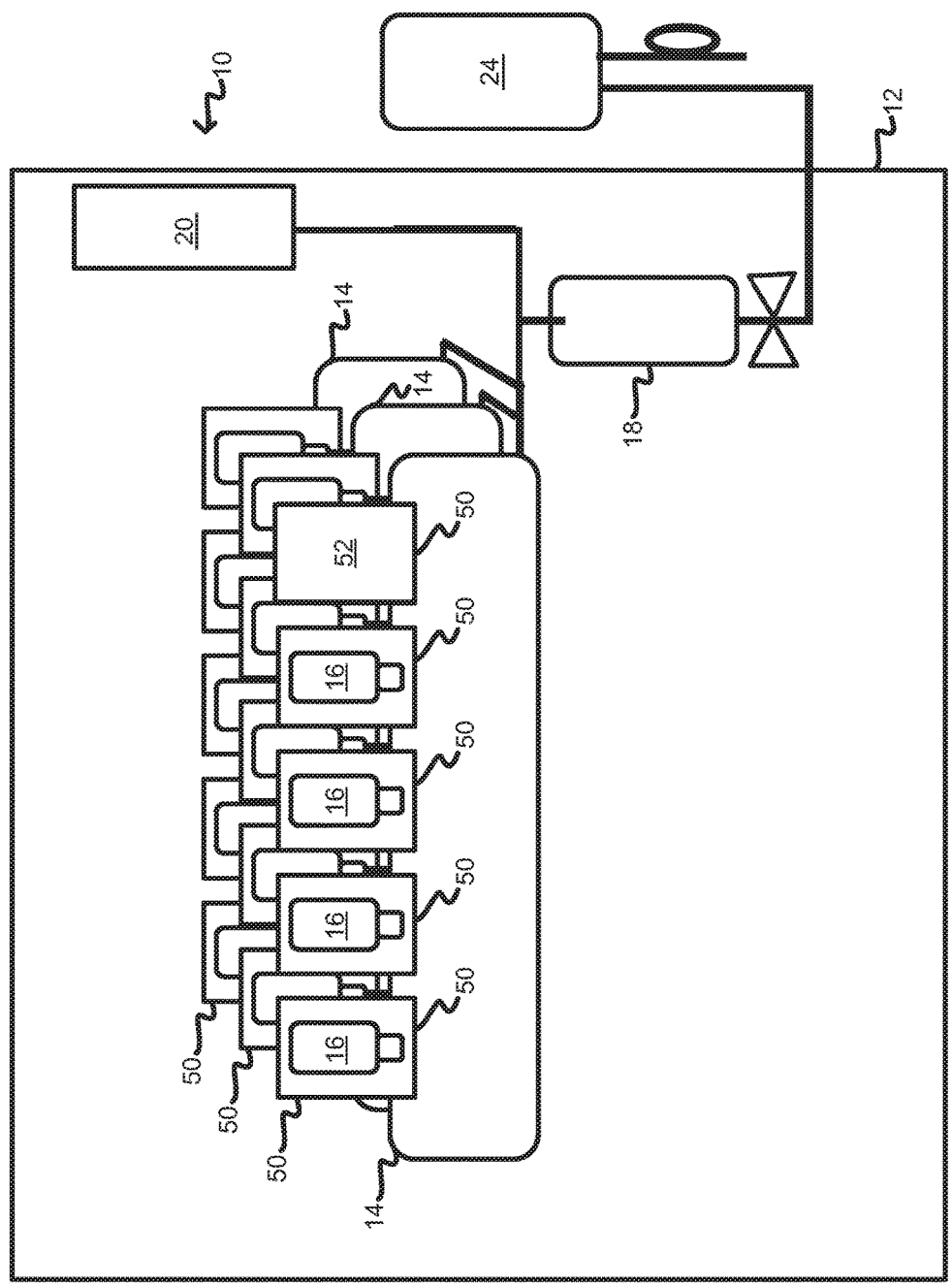
FIG. 3 depicts a third example representative block diagram of a compounder.

FIG. 3 depicts another example embodiment of a compounder 10. As shown, the compounder 10 includes a number of manifolds 14. As previously mentioned, other embodiments may include a greater or lesser number of manifolds 14. As shown, all of the manifolds 14 are arranged in parallel. This arrangement may help to increase throughput of the compounder 10 since more than one manifold 14 may deliver fluid to a mixing chamber 18 simultaneously. This may further be advantageous for a variety of other reasons. For instance, such an arrangement would allow reservoirs 16 containing contraindicated drugs to be placed on separate manifolds 14. It would allow for some reservoirs 16 to be contained in a different controlled environment (e.g. different temperature zones) within the compounder 10 housing 12. Additionally, it may allow for manifolds 14 to be made of a variety of materials. Thus, reservoirs 16 may be placed on manifolds 14 made from compatible materials.

As shown, all of the manifolds 14 are plumbed into the same mixing chamber 18. In some embodiments, each manifold 14 may be associated with its own mixing chamber 18.

In the embodiment depicted in FIG. 3, each of the reservoirs 16 is enclosed within a reservoir receptacle or cartridge 50. It may be desirable to enclose a reservoir 16 within a cartridge 50 if the reservoir 16 contains hazardous contents. In applications where the compounder 10 is for use in the compounding of pharmaceuticals, it may be desirable to have various drugs enclosed in a cartridge 50. For example, some drugs, such as those used in chemotherapy applications, may give off dangerous vapors or may be harmful if they contact a handler. The cartridge 50 may be used to seal the drug containing reservoir 16 such that vapors and/or fluids may not exit the cartridge 50 and pose a hazard to users of the compounder 10. In some embodiments, the cartridge 50 itself may seal the reservoir 16 from the surrounding environment. In some embodiments, the cartridge 50 may contain a closure which may facilitate sealing. The cartridge 50 may then interface with the manifold 14 such that the cartridge 50 may be docked on the manifold 14

In other embodiments, the cartridge 50 may cooperate with one or more additional component to create a seal. Some embodiments may use a cartridge 50 similar to the vial receptacle, shown and described in U.S. Pat. No. 8,158,102, issued Apr. 17, 2012 and entitled SYSTEM, DEVICE, AND METHOD FOR MIXING A SUBSTANCE WITH A LIQUID, which is incorporated herein by reference in its entirety. In such embodiments, the cartridge 50 may be spiked with a spike receptacle in a vial spike assembly also as shown and described in just referenced U.S. Pat. No. 8,158,102.

For some applications, the reservoirs 16 need not be enclosed and sealed using a cartridge 50. For example, it may not be necessary for drugs used by a compounder 10 which pose less of a handling hazard to be sealed. In such instances, bare reservoirs 16 may be docked on the manifold 14. These reservoirs 16 may come in a number of different styles, types, sizes or dimensions. In some embodiments, adapter members may also be included for each reservoir 16 variety. The adapter members may fit around and/or over a portion of the reservoirs 16. The adapter members may also have a standardized connecting feature or fitting. The connecting feature may allow the ports of the manifolds 14 to be standardized to a single size, geometry, etc. Thus, a reservoir 16 with the proper adapter attached may be placed on any suitable manifold 14 port regardless of the dimensions, type, style, etc. of the reservoir 16. Alternatively, manifolds 14 may include dedicated ports for each variety of reservoir 16 or the compounder 10 may include designated manifolds 14 for each variety of reservoir 16. In other embodiments, the manifolds 14 may interface with specifically designed reservoirs 16. This may ensure that only reservoirs 16 made for use in the compounder 10 are able to be used with the compounder 10.

In addition to reservoirs 16 coming in a number of different styles, types, sizes or dimensions, the stoppers (not shown) used in these reservoirs 16 may also vary. The stoppers may affect the distance that a spike for the reservoir 16 may penetrate into the interior volume of that reservoir 16. Since, for example, it would be desirable that an outlet spike for a reservoir 16 be located toward the bottom of the reservoir volume 16, in some embodiments, adapter members may similarly be included for each stopper variety. Such adapters may function similarly to those described above, however, may also ensure that the reservoir 16 is located at a distance from the manifold 14 which ensures the spike is at a suitable location within the reservoir volume when the reservoir 16 is docked to a manifold 14.

It may be desirable that the reservoir-manifold interface or manifold 14 port be made aseptic or sterilizable for certain compounder 10 applications. In the compounding of pharmaceuticals, this may be particularly desirable. In some embodiments, the compounder 10 may include one or more cleaning cartridge 52. In the embodiment depicted in FIG. 3, a cleaning cartridge 52 is docked to the farthest right port of the foremost manifold 14. In some embodiments, a steam line (not shown) may be plumbed into communication with a cleaning cartridge 52. The cleaning cartridge 52 may be placed over the desired manifold 14 port and steam may be allowed to fill the cleaning cartridge 52. This steam may sterilize the manifold 14 port. During cleaning with the cleaning cartridge 52, any valves for fluid pathways leading to or from a selected manifold 14 port may be closed.

Alternatively, the compounder 10 may be configured to move an entire manifold 14 to a sterilizing chamber in the housing 12 of the compounder 10. This may, for example, be accomplished with a gantry such as the gantry 30 shown in FIG. 2. In some embodiments, the sterilizing chamber may be a steam chamber. Such a sterilizing scheme may, however, slow throughput of the compounder 10.

Figure 4:
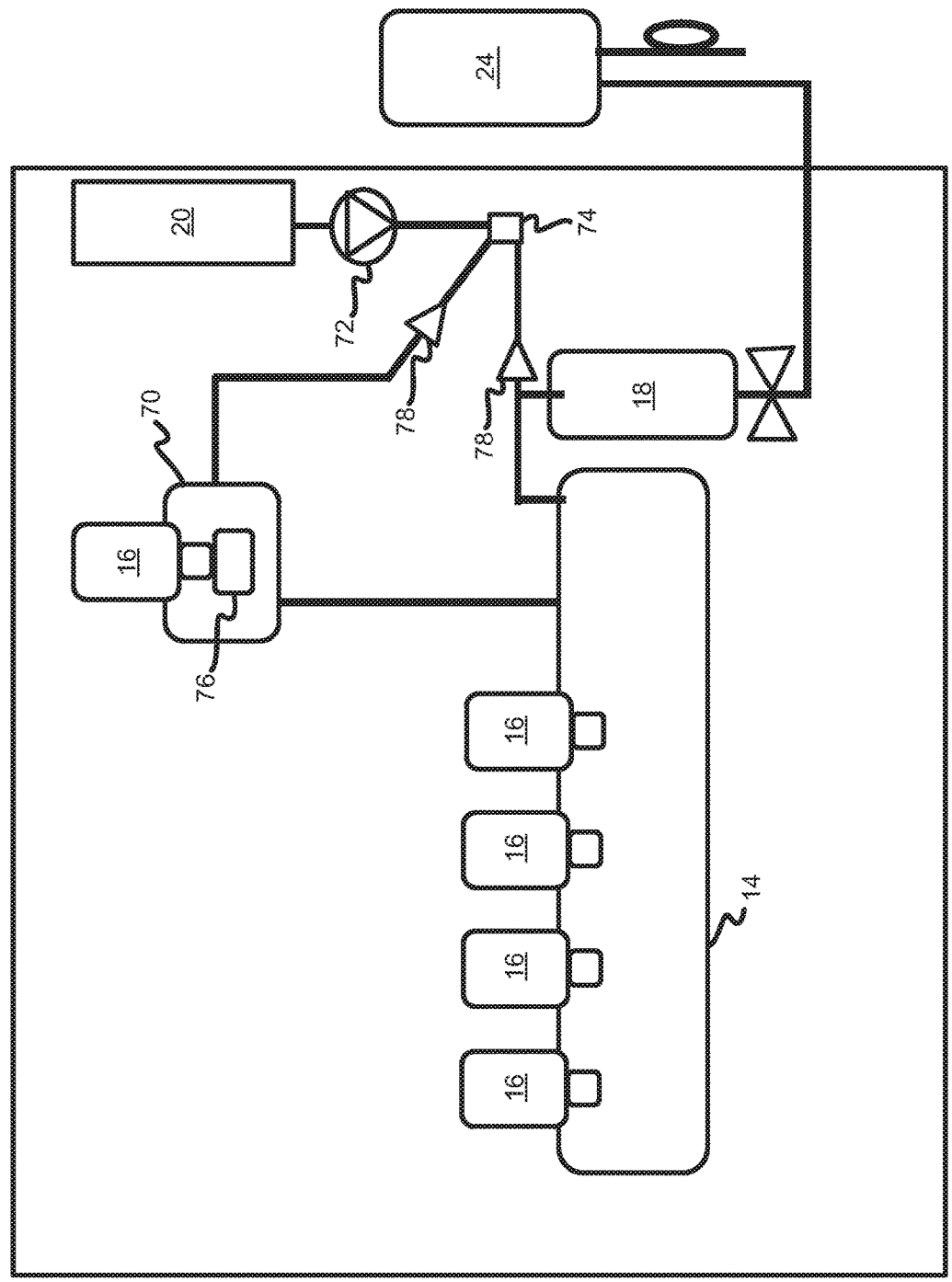
FIG. 4 depicts a representation diagram of a compounder which is configured to reconstitute a drug which is in a powdered form.

In some embodiments, materials used by a compounder 10 may not come in a liquid form. For example, some drugs may come in a powdered or lyophilized form. Such drugs may need to be reconstituted before compounding or administration to a patient. In some embodiments, such materials may be reconstituted by a user before being provided to a compounder 10. In other embodiments, a compounder 10 may be configured to reconstitute the material. FIG. 4 depicts a representation diagram of a compounder 10 which is configured to reconstitute a drug which is in a powdered form.

As shown, the compounder 10 includes a manifold 14. A number of reservoirs 16 are docked on the manifold 14. The manifold 14 in FIG. 4 is also in communication with a reconstituting component 70. Some embodiments may include additional reconstitution components 70. As shown, a reservoir 16 is docked on the reconstituting component 70. The reservoir 16 on the reconstituting component 70 may include a powdered drug.

As shown, the reconstituting component 70 may also be placed into communication with a diluent source 20. As shown, diluent may be pumped from the diluent source 20 using a diluent pump 72. In other embodiments, fluid may flow from the diluent source 20 by means of a gravity feed. In other embodiments, fluid may be compelled to leave the diluent source 20 by any number of other suitable means. Such suitable means may include, but are not limited to, creating a positive pressure in the diluent source 20 container, creating a vacuum downstream of the diluent source 20, squeezing or collapsing the diluent source 20 container, etc.

In the example embodiment, when a diluent valve 74 is appropriately actuated, the diluent may flow to the reconstitution component 70. As shown, check valves 78 are included to ensure that no diluted medication may enter the diluent lines. The reconstitution component 70 may reconstitute the drug. In some embodiments, this may be accomplished by pumping diluent into the reservoir 16. The reservoir 16 or diluent in the reservoir 16 may be actively agitated to encourage the powdered drug to go into solution quickly. In some embodiments, the diluent may be pumped back and forth between the reservoir 16 and a reconstitution chamber 76 in the reconstitution component 70 in order to fully reconstitute the drug.

In some embodiments, the reconstituted solution may be agitated for an empirically derived predetermined period of time for each drug. The period of time may be a tested period of time sufficient for the powdered drug within the reservoir 16 to go into solution plus an additional margin. In some embodiments, the reconstitution component 70 may include one or more sensor (not shown). For example, the reconstitution component 70 may include a conductivity probe which may be used to detect whether or not the drug has fully gone into solution. In some embodiments, the reconstitution component 70 may include an optical sensor which monitors for particulates which would indicate that the drug has yet to fully go into solution. In some embodiments, the reconstitution component 70 may include one or more sensor to monitor the volume of diluent used to reconstitute the drug. The reconstitution component 70 may also include one or more sensor which may measure the volume of the reconstituted drug. Such an arrangement would allow a controller to compare the volume of diluent to the reconstituted drug volume to determine the drug concentration.

In some embodiments the reconstituting component may include a reconstituting cassette similar to as described in U.S. Pat. No. 6,210,361, issued Apr. 3, 2001 and entitled SYSTEM FOR DELIVERING INTRAVENOUS DRUGS, which is incorporated herein by reference in its entirety. Such a cassette may also be used in place of the manifolds 14 described herein.

Once the drug has been reconstituted, it may be allowed to flow to a fluid path of a manifold 14 and on to a mixing chamber 18. In other embodiments, the drug may flow from the reconstitution component 70 to the mixing chamber 18. In other embodiments, other non-liquid materials may be reconstituted and mixed by a compounder 10. For example, in embodiments where the compounder 10 is not used in a pharmaceutical application, the compounder 10 may reconstitute powdered drink mix.

Figure 5:
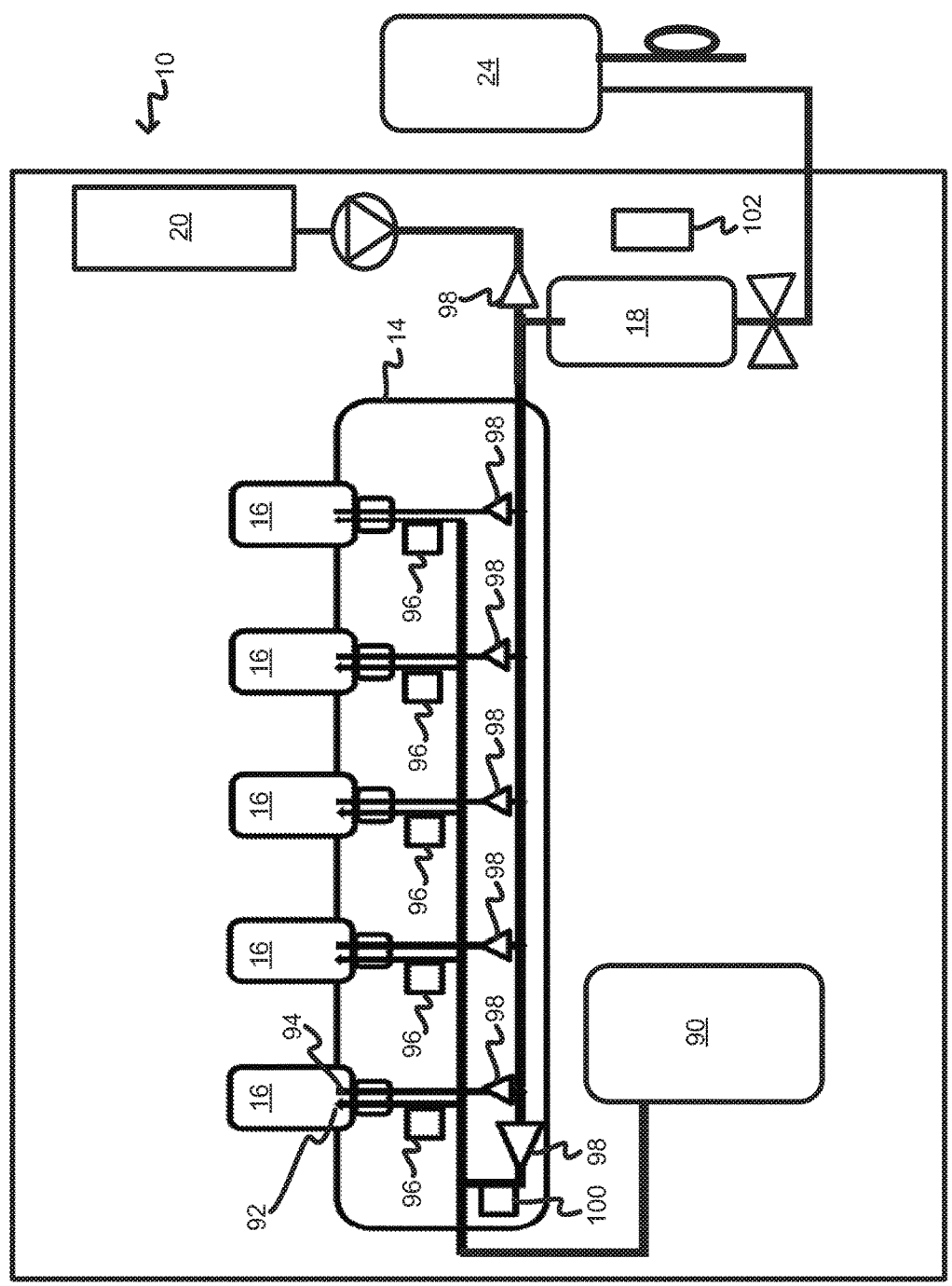
FIG. 5 depicts a representational diagram of a compounder in which various flow paths of a manifold are depicted.

FIG. 5 depicts a representational diagram of a compounder 10 in which various flow paths of a manifold 14 are depicted. As shown, each reservoir 16 docked on the manifold 14 has been spiked such that it may be placed in communication with the various fluid pathways of the manifold 14. In the example embodiment, each reservoir 16 is spiked with an inlet 92 and an outlet 94. The inlet 92 and outlet 94 may be two separate needles or a double lumen needle in some embodiments. In other embodiments only a single needle may be used. In still other embodiments, more than two needles may be used.

As shown, the manifold 14 is in communication with a clean air reservoir 90. The clean air reservoir 90 in the example embodiment is a pressurized tank of clean, medical grade air. In other embodiments, the clean air reservoir 90 may differ. For example, in some embodiments, the clean air reservoir 90 may be part of a clean air system included in the compounder 10. In such embodiments, the clean air reservoir 90 may be an accumulator for a compressor pump (not shown). The pump may pump in ambient air. This air may pass through appropriate filters, dryers, etc. to ensure it is suitable for use in the compounder 10.

Clean air from the clean air reservoir 90 may selectively be routed into desired reservoirs 16 on the manifold 14. To facilitate this, the manifold 14 may include a number of valves 96. The valves 96 may open and close the fluid path between the clean air reservoir 90 and inlet 92 for each reservoir 16. When the fluid pathway is open, clean air may flow into the reservoir 16 from the pressurized clean air reservoir 90. This may create a positive pressure in the reservoir 16 and force fluid out of the reservoir 16 through the outlet 94. In some embodiments, the volume of air which may flow into a reservoir 16 may be controlled so as to displace a desired amount of fluid from the reservoir 16. This may, for example, be accomplished by cycling the valves 96 associated with each reservoir 16 to achieve a desired flow rate. It may be desirable that the inlet 92 is configured to be positioned near the top of the interior volume of the reservoir 16 when the reservoir 16 is spiked. This may help to minimize concern for creation of air bubbles when forcing fluid out of the reservoir 16. It may also be desirable that the outlet 94 be near the bottom of the reservoir 16. This may help to ensure that all of the fluid within the reservoir 16 may be used by the compounder 10. As mentioned above, not all embodiments may create a positive pressure in a reservoir 16 to draw fluid out of the reservoir 16. The compounder 10 may be configured to use any other suitable means of drawing fluid from a reservoir 16 such as those mentioned above.

The valves 96 may be any suitable variety of valve. In some embodiments, the valves 96 may be solenoid type valves. In other embodiments, the valves 96 may be bi-stable valves such as those disclosed in U.S. Provisional Application Ser. No. 61/844,202, filed Jul. 9, 2013 and entitled VALVE APPARATUS AND SYSTEM; U.S. patent application Ser. No. 14/327,206, filed Jul. 9, 2014 and entitled VALVE APPARATUS AND SYSTEM and U.S. Provisional Application Ser. No. 62/091,351, filed Dec. 12, 2014 and entitled MODULAR VALVE APPARATUS AND SYSTEM, each of which is incorporated herein by reference in its entirety.

Once fluid travels from the reservoir 16 through the outlet 94, it may pass through a check valve 98. The fluid may then flow to a mixing chamber 18. As shown, each outlet includes a check valve 98. This may ensure that fluid from one reservoir 16 may not enter another reservoir 98 through that reservoir's 16 outlet 94. Additionally, it may ensure that during flushing of the manifold 14, fluid may not enter any of the reservoirs 16.

As shown in FIG. 5, the manifold 14 is configured such that clean air from the clean air reservoir 90 may be used to flush the manifold 14. To flush the manifold 14, a flush valve 100 may be opened. Opening the flush valve 100 may place the fluid pathways for fluid leaving the reservoirs 16 into communication with clean air reservoir 90. Pressurized air may then flow through these fluid pathways flushing out remaining fluid. As shown in the example embodiment, a check valve 98 is also included downstream from the flush valve 100 to preclude fluid from the reservoirs 16 from flowing back to the clean air reservoir 90 or other undesired fluid pathways of the manifold 14. The flush valve 100 may be any suitable type of valve. In some specific embodiments, the flush valve 100 may be a bi-stable valve such as those disclosed in U.S. Provisional Application Ser. No. 61/844,202, filed Jul. 9, 2013 and entitled VALVE APPARATUS AND SYSTEM; U.S. patent application Ser. No. 14/327,206, filed Jul. 9, 2014 and entitled VALVE APPARATUS AND SYSTEM and U.S. Provisional Application Ser. No. 62/091,351, filed Dec. 12, 2014 and entitled MODULAR VALVE APPARATUS AND SYSTEM, each of which is incorporated herein by reference in its entirety.

In alternative embodiments, diluent from a diluent source 20 may be pumped through these fluid pathways to flush out any remaining fluid. In other embodiments, the manifold 14 may be flushed with both clean air from the clean air reservoir 90 and diluent from the diluent source 20.

In some embodiments, the manifold 14 may instead or additionally be put into communication with a steam source or other hot fluid source and be periodically flushed with fluid from this source for cleaning purposes. In some embodiments, when a reservoir 16 is spent, steam or other suitable hot fluid may be routed through the manifold 14 and into the reservoir 16. This may be done to clean the manifold 14 port without removing the spent reservoir 16.

In some embodiments, any fluid from a manifold 14 flushing may be directed to a dump location or flush discard reservoir. Additionally, in some embodiments, after a manifold 14 or manifold 14 port is cleaned, the manifold 14 may be flushed to remove dead pathogens or other matter.

In some embodiments, the manifold 14 may include additional components. For example, the manifold 14 may include an air bubble detector (not shown). The manifold 14 may also include an occlusion detector (not shown). The manifold 14 may also include sensors (not shown) at each manifold 14 port which sense whether a reservoir 16 has been docked on that port. In some embodiments, such sensors may also sense whether a reservoir 16 is improperly docked on a port.

As mentioned above, fluid from the reservoirs 16 may travel from the manifold 14 to a mixing chamber 18. A mixing chamber 18 may be used to mix fluid from one or multiple reservoirs 16 with diluent from a diluent source 20. In various embodiments, the size of the mixing chamber 18 may differ. In some embodiments, the mixing chamber 18 may be sized such that it may be filled and dispensed a plurality of times to fill a destination reservoir 24. In some embodiments, the mixing chamber 18 may be sized such that it need only be filled and dispensed a single time to fill a destination reservoir 24. In some embodiments, the mixing chamber 18 may be a reusable component of the compounder 10. That is, the same mixing chamber 18 may be used repeatedly as multiple pharmaceutical compounds are compounded by the compounder 10. In other embodiments, the mixing chamber 18 may be a limited (e.g. one time) use disposable which may be replaced after each pharmaceutical compound is compounded by the compounder 10. In such embodiments this replacement may be done automatically.

The mixing chamber 18 may be monitored by one or more sensor 102. The one or more sensor 102 may track the volume of fluid entering the mixing chamber 18. Thus the one or more sensor 102 may be used to ensure that fluids entering the mixing chamber 18 are combined in proper concentrations. In some embodiments, the one or more sensor 102 may be selected from one or a combination of the following: an acoustic volume sensor, a capacitance sensor, an ultra-sonic sensor, a range finder etc. Additionally or alternatively, in some embodiments, a piezoelectric jet may be used to control the flow of fluid into the mixing chamber 18.

In some embodiments, the mixing chamber 18 may be similar to a drip chamber. In such embodiments, the one or more sensor 102 may include a camera which monitors fluid in the mixing chamber 18. In such embodiments, the camera may measure the volume of fluid entering the mixing chamber 18 to determine when a proper amount of a fluid has entered the mixing chamber 18. In some embodiments, the camera may also be used to determine flow rate of fluid into the mixing chamber 18. In some embodiments, the camera may be used to determine when to halt fluid flow into the mixing chamber 18 or when to deliver fluid in the mixing chamber to a destination reservoir 24.

Figure 6:
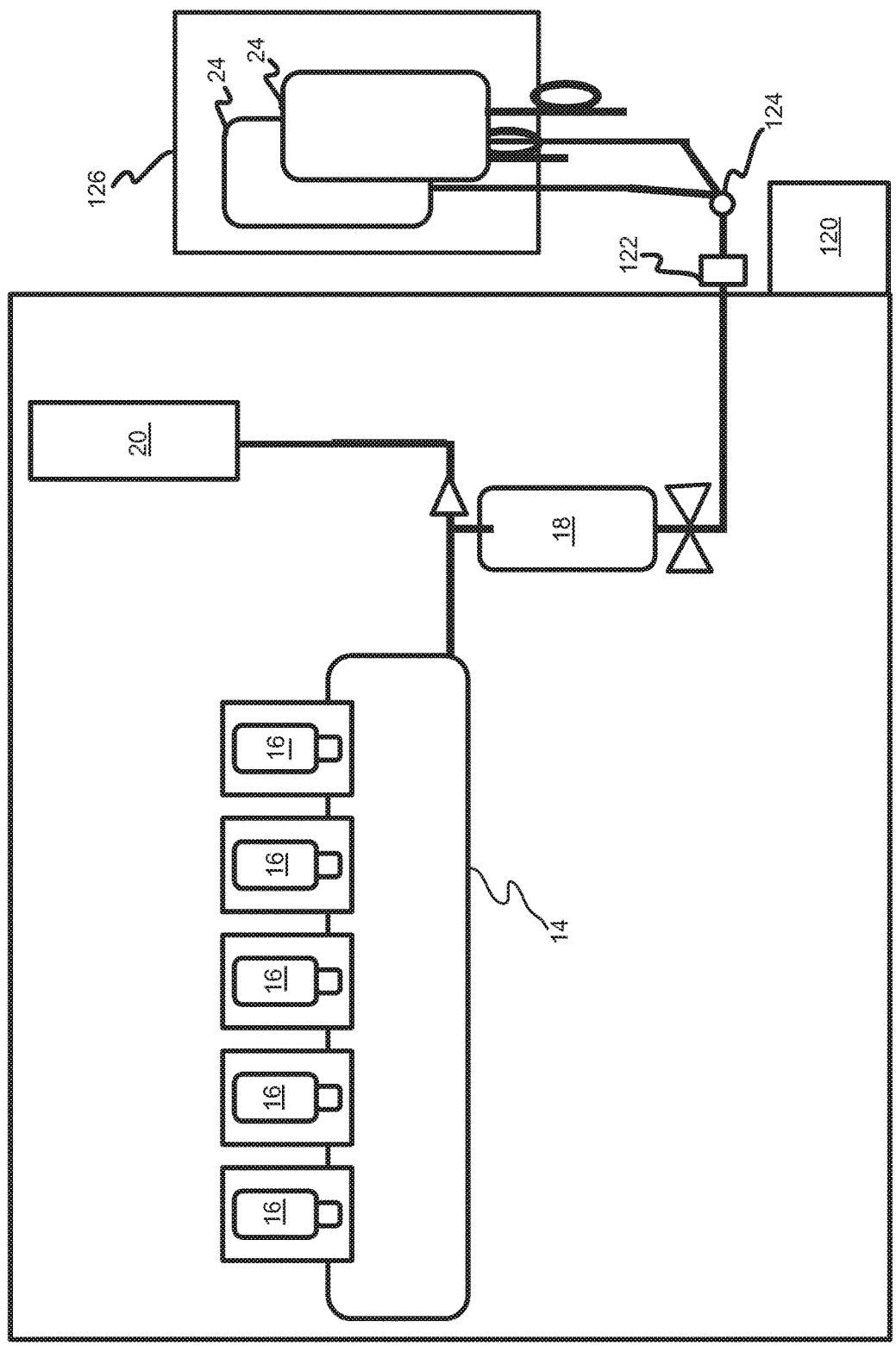
FIG. 6 depicts a representational embodiment of a compounder in which a labeler and destination reservoir connection port are also shown and included.

FIG. 6 depicts a representational embodiment of a compounder 10 in which a labeler 120 and destination reservoir connection port 122 are shown. As shown, the reservoir connection port 122 may serve as the interface between the compounder 10 and a destination reservoir 24. A destination reservoir 24 may couple to a reservoir connection port 122 such that the compounder 10 is placed in fluid communication with the destination reservoir 24. The reservoir connection port 122 may be a part of the compounder 10 and may be reused each time a destination reservoir 24 is attached. As shown, there are two destination reservoirs 24 attached to the connection port 122 by means of a y-site connector 124. In some embodiments, the y-site connector 124 may be included as part of the connection port 122. In other embodiments, suitable connectors may be included to allow additional destination reservoirs 24 to be connected. Alternatively, a manifold (not shown) may be included to route fluid to one of plurality of desired destination reservoirs 24.

Connecting multiple destination reservoirs 24 may be desirable if the compounder 10 is commanded to produce a large volume of the same pharmaceutical compound because it may help to increase throughput. This may be so because the compounder 10 would not need to stop to allow a user to time to disconnect a destination reservoir 24, clean the connector port 122, and connect another destination reservoir 24. In a preferred embodiment, the connection port 122 may be a standard fitting which may connected to any of a variety of destination reservoirs 24. In some embodiments, or for some destination reservoirs 24 various adapters may be used when coupling the connection port 122 to a destination reservoir 24.

Before a destination reservoir 24 may be connected to the compounder 10, it may be desirable that the connection port 122 be sterile. In some embodiments, the connection port 122 may come as a sterile disposable which is replaced as needed. In other embodiments, the connection port 122 may be configured to be sterilizable. Any suitable means of sterilizing the connection port 122 may be used. The connection port 122 should be made of a material which will not degrade with repeated sterilization. In some embodiments, the connection port 122 may be sterilized by means of a steam bath or steam jet. In some embodiments, the connection port 122 may be cleaned with ultra-violet light. In some embodiments, radiation may be used to sterilize the connection port 122. In some embodiments, the connection port 122 may be made of metal and may be inductively heated to a suitable temperature for sterilization. In other embodiments, the connection port 122 may be heated by other means for sterilization purposes. In some embodiments, any combination of suitable means to sterilize the connection port 122, including though not limited to those described above, may be used.

As shown, the compounder 10 may also include or interface with a scale or load cell 126. The load cell 126 may be configured as a shelf, tray, holder, or the like for the destination reservoir 24 during filling of the destination reservoir 24. The load cell 126 may be used for checking the compounded solution with by gravimetric means. After the destination reservoir 24 has been filled with the proper volume of compounded solution, the weight of the destination reservoir 24 as measured by the load cell 126 may be checked against an expected weight. If the weight of the destination reservoir 24 is within a predetermined range of the expected weight, the compounder 10 may signal the destination reservoir 24 is ready for use and may be removed. If the weight of the destination reservoir 24 is outside of the predetermined range, the compounder 10 may generate an error and indicate that that destination reservoir 24 should not be used.

Once the compounder 10 has filled a destination reservoir 24 with the compounded drug, the compounder 10 may generate a label for the destination reservoir 24. This label may be generated by a labeler 120 included as a part of the compounder 10. The labeler may label the destination reservoir 24 with one or more of a unique identifier, compound name, medications used in the compound, an administration profile, a patient identifier, the destination reservoir 24 weight, a use by time or date, and so on. The labeler 120 may produce any suitable variety or label, for example, adhesive backed information print out, barcode, RFID, magnetic strip, etc. In some embodiments, a customer may chose which type of labeler 120 they would like included on a compounder 10. This may be desirable because it would allow a customer to pick a labeler 120 which would best interface with their institution. In some embodiments, the labeler 120 may also place the label on the destination reservoir 24 in an automated fashion. In other embodiments, the labeling of a destination reservoir 24 may be done manually. As mentioned, in some embodiments, the label may include use by information. In embodiments where the label must be read or scanned by another device, the device may notify the user that the destination reservoir 24 contains medication with is past is use by time or date. In some embodiments, the device may disallow usage of the destination reservoir 24.

In some embodiments, the compounder 10 may also generate a report for each compounded pharmaceutical. In such embodiments, these reports may be printed via a labeler 120 or may be saved electronically and later downloaded from the compounder 10.

Figure 7:
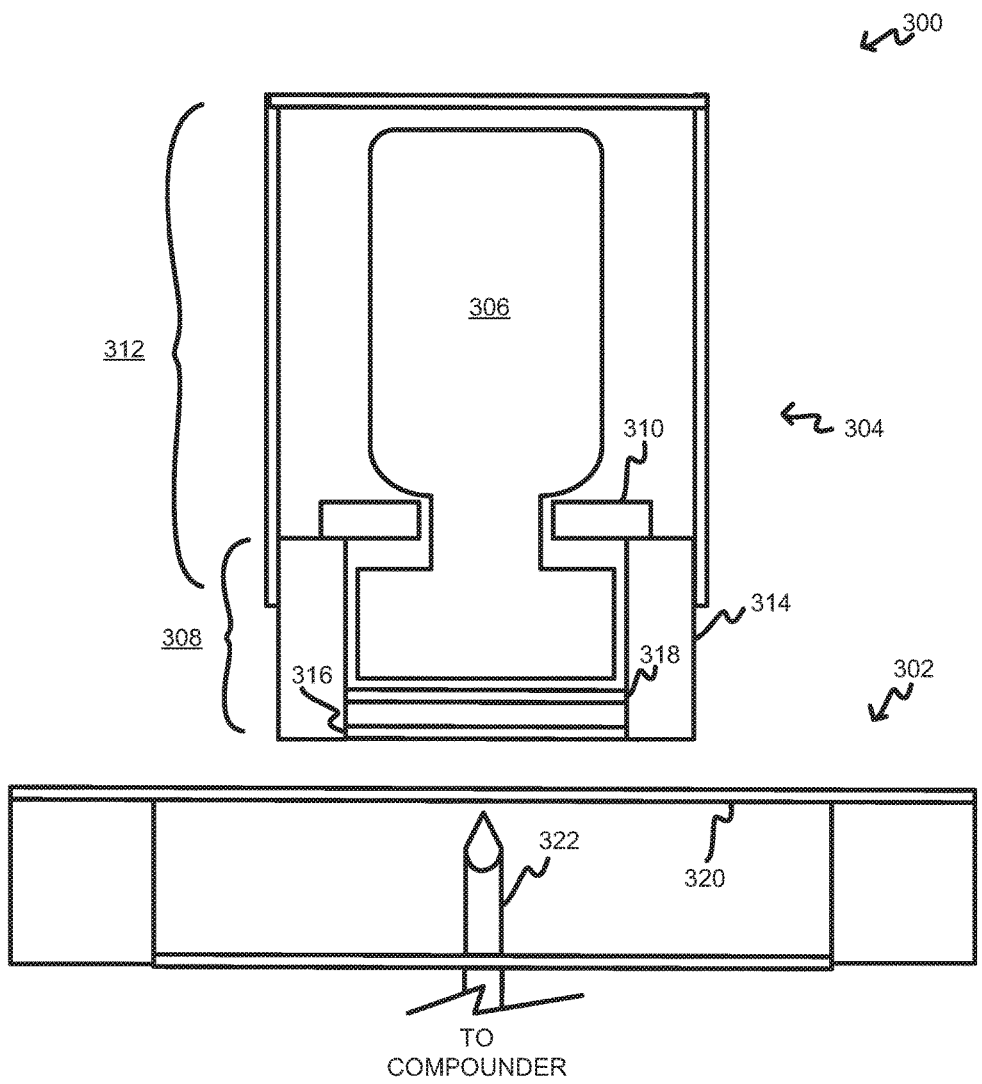
FIG. 7 depicts a representational embodiment of a drug reservoir containment assembly.

FIG. 7 depicts a representational example embodiment of a drug reservoir containment assembly 300 and a compounder dock 302. As shown, the drug reservoir containment assembly 300 is not in place on the compounder dock 302. As mentioned, the drug reservoir containment assembly 300 may be used to ensure that any hazardous vapors or substances are contained and prevented from entering the ambient environment.

A drug reservoir containment assembly 300 may generally include one or more enclosing structures or housing sections and an adapter which allows the enclosing structures to receive a plurality of reservoirs (e.g. vials, bags, etc.). The enclosing structures and adapter may mate and or assemble together to form a sealed or air-tight interior volume where the drug reservoir may be held or retained. The containment assembly 300 may include one or more windows which allow a user to view the contents of the containment assembly 300. The containment assembly 300, in some embodiments, may be clear, translucent, or transparent to allow a user to view the contents of the containment assembly, or to generally view the interior of the containment assembly 300.

The adapter may be a separate component or alternatively may be an integral part of an enclosing structure. Suitable sealing members (gaskets, o-rings, etc.) may be included to ensure that the drug reservoir containment assembly 300 is sealed from the environment when assembled. At least one enclosing structure may include one or more septum which may be pierced by a spike of a compounder. The one or more septum may be disposed in a channel which extends from a proximal end of an enclosing structure to a distal end of the enclosing structure and may form a barrier between the proximal and distal end of the channel. The septum may be made of a self healing material and allow for a seal to be maintained when a drug reservoir containment assembly 300 has been spiked during use. Additionally, a portion of a drug reservoir containment assembly 300 may act as a sealed receiving volume for any hazardous substances or vapors which may escape a drug reservoir. In such embodiments, the receiving volume may be negatively pressurized and may be rigid or expandable. In various embodiments, at least a portion of the enclosing structure or housing section having the receiving volume may be of variable volume.

As shown in the specific example in FIG. 7, the drug reservoir containment assembly 300 is a vial containing assembly. Similar containment assemblies may be used for other types of drug reservoirs. The example containment assembly 300 includes a vial receiving assembly 304 which receives a vial 306. The vial 306 is enclosed and sealed within the vial receiving assembly 304.

As shown, the receiving assembly 304 includes two enclosing portions: a dock interface portion 308 and a variable volume housing portion 312. The receiving assembly 304 also includes an adapter 310. The dock interface portion 708 interfaces with a compounder dock 302 and may include an interface structure 314. The interface structure may be a rigid body which surrounds the stopper and crimp of a vial 706. Additionally, the interface structure 314 may include a feature which locks into or mounts into the compounder dock 702 in any of a variety of ways. In various embodiments, the interface structure 314 may thread into, snap into, magnetically mate, bayonet mount into, or otherwise be secured into the compounder dock 302.

An interface portion 308 of a drug reservoir receiving assembly 300 may include at least one septum. This septum may span an opening in the interface portion 308 creating an elastomeric seal. In the example embodiment shown in FIG. 7, the interface portion 308 includes a first septum 316 and a second septum 318. Other embodiments may include a greater or lesser number of septa. These septa 316, 318 may be made an elastomer, rubber, a flexible polymer, resilient material, or any elastomeric or self healing material which is capable of being pierced by a needle 322 and maintaining a seal and wiping the needle when the needle 322 is withdrawn.

The example receiving assembly 304 also includes an adapter 310 as mentioned above. The adapter 310 may fit around a portion of a vial 306 allowing the vial 306 to coupled into a standard interface portion 308. In the example embodiment, the adapter 310 is shown around the neck of the vial 306. In other embodiments, the adapter 310 may fit around another portion of the vial 306 or may be included as part of the interface portion 308. Different adapters 310 may be used depending on the vial type 306. Alternatively, the adapter 310 may be standard and include a variable aperture or cinching mechanism which allows the adapter 310 to adapt itself to a range of different vial 306 types. In some specific embodiments, the adapter 310 may be a collar which fits around the vial 306 neck. In some embodiment, the adapter 310 may be include two pieces which may be coupled together around a suitable portion of a vial (e.g. the neck). In such embodiments, the pieces may snap, or friction fit together, be bonded (adhesive, solvent, etc.) together, magnetically couple, or couple in any other manner which would be known to one skilled in the relevant art. The adapter 310 may include a hole or gap to vent gases emanating from the spike region to the variable volume of the variable volume housing portion 312 (e.g., see the pass-through 336 shown in FIG. 10).

The variable volume housing portion 312 of the receiving assembly 304 may fit around the portion of the vial 306 or medication reservoir not housed by the interface portion 308 or adapter 310. Thus the vial 306 may be completely enclosed and sealed from the surrounding environment. In the example embodiment, the variable volume housing portion 312 houses the vial body. A variable volume housing 312 may be made of an elastomeric or stretchable material or may include at least one flexible or expandable segment or feature (e.g. pleats of a bellows). Additionally, it may be desirable that the variable volume housing portion 312 be made of a durable and substantially impermeable material.

The variable volume housing 312 may function as a protective sleeve or jacket for the medication vial receiving assembly 304 and in concert with the septa 316, 318 prevent any leakage of potentially hazardous fluid into the environment. If pressure or vapors escape from the vial 306, the escaping fluid may be captured and retained within the variable volume housing 312. This may increase the volume of the variable volume housing 312. The material of the variable volume housing 312 may allow the variable volume housing 312 to expand or inflate to accommodate the escaping fluid if necessary. In this manner, a variable volume housing 312 may allow for any fluid escaping from a medication vial 306 to be contained and sealed within the vial receiving assembly 304.

The interior volume of the variable volume housing 312 may be at ambient pressure when a drug reservoir containment assembly 300 is docked on a compounder dock 302. Alternatively, a drug reservoir containment assembly 700 may include a port which allows the interior volume of the variable volume housing to be lowered below ambient pressure or emptied of fluid after a vial 306 is installed. This may minimize any stretching of the variable volume housing 312 material in the event that any fluid escapes the vial 306.

The compounder dock 302 may include cooperating receiving structures which mate with a mating feature included on the interface portion 308 of a drug reservoir containment assembly 300. Any suitable mating arrangement may be used. Additionally, the compounder dock 302 shown includes a septum 320. In other embodiments, multiple septa or no septum may be included on the compounder dock 302. The septum 320 may be a replaceable component in some embodiments. Similar to the septa 316, 318 described in relation to the drug reservoir containment assembly 300, the septum 320 (or septa) of a compounder dock 302 may be made of an elastomeric or self healing material. A spike 322 may also be included in a compounder dock 302. The spike may pierce through the septum or septa of the dock 302 and containment assembly 300 into the drug reservoir such that fluid may be drawn out of or introduced into the reservoir. Though only one spike 322 is shown in the example embodiment, other embodiment may include multiple spikes as described above.

Figure 8:
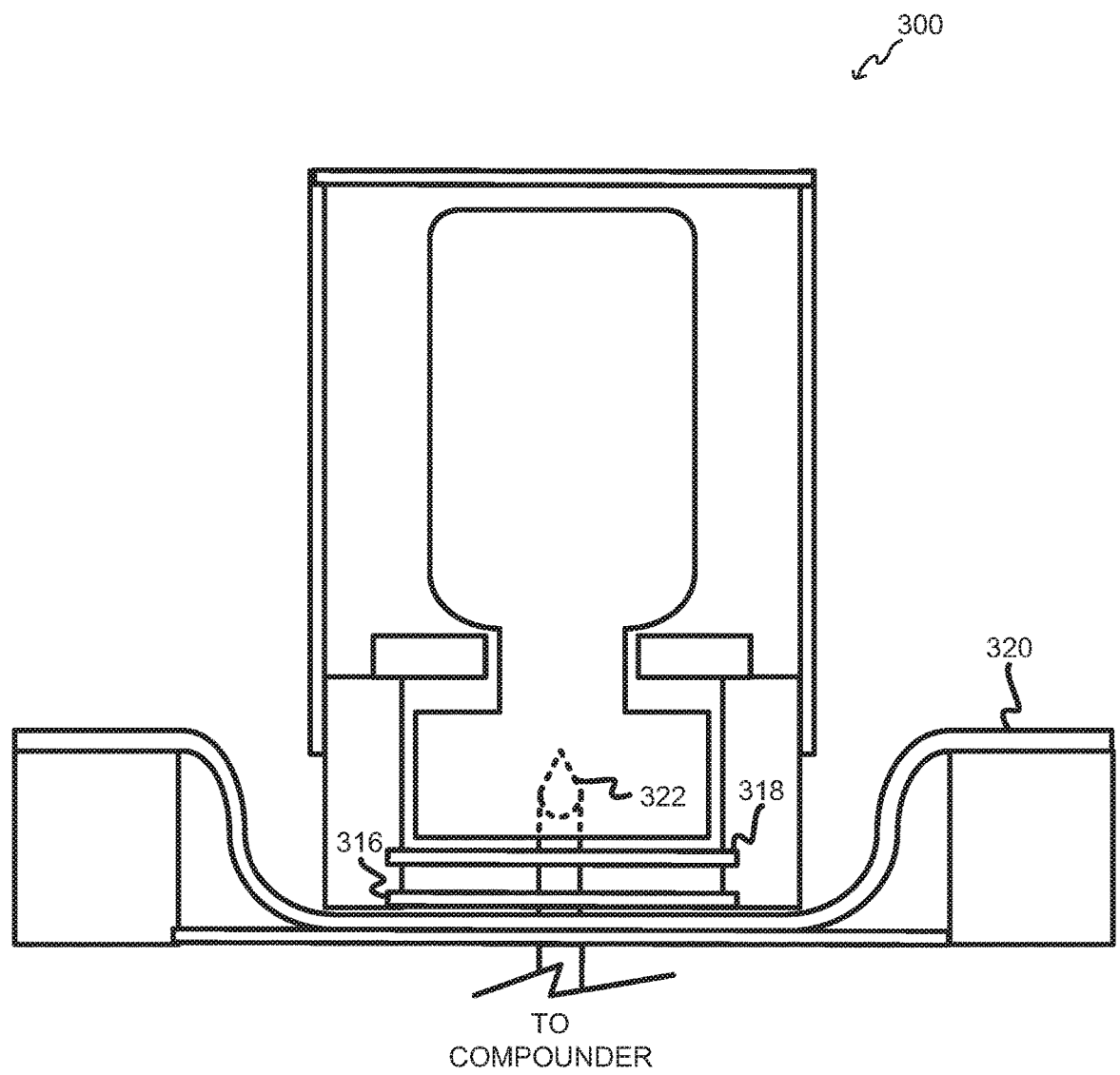
FIG. 8 depicts a representational embodiment of a drug reservoir containment assembly.

FIG. 8 depicts the representational example embodiment of a drug reservoir containment assembly 300 and a compounder dock 302 of FIG. 7 with the containment assembly 300 docked to the compounder dock 302. Substances are contained and prevented from entering the ambient environment. As shown, the containment assembly 304 has been lowered down onto the spike 322 of the dock 302 such that the spike 322 has pierced through the septa 316, 318, and 320 and into the vial 306.

In addition to providing a seal against any potentially hazardous substances, the septa 316, 318 of the containment assembly 300 may provide additional benefits. For example, as the containment assembly 300 is removed from the compounder dock 302, the spike 322 will be pulled through the septa 316, 318. Thus the septa 316, 318 serve to wipe the spike 322 when the spike 322 is withdrawn. Any fluid wiped from the spike 322 will be kept on the interior side of the septa 316, 318, facilitating containment. The compounder dock 302 septum 320 may act as a cover for the spike 322 keeping the spike 322 from being exposed. This may aid in the prevention of contamination and may facilitate cleaning as only the top face of the septum 320 may need to be cleaned between uses.

Figure 9:
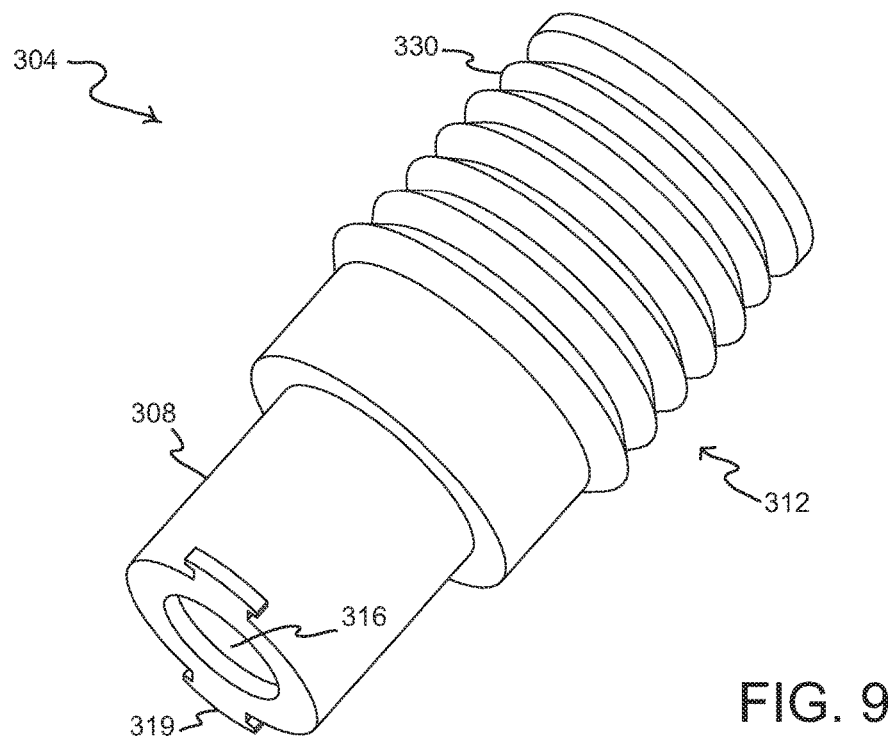
FIG. 9 depicts an embodiment of a vial containment assembly.

FIG. 9 depicts a specific example embodiment of a vial receiving assembly 304. As shown, only the interface portion 308, septum 316, and the variable volume housing portion 312 are visible in FIG. 9. In the example embodiment, the variable volume housing portion 312 includes a bellows 330 which may be in a collapsed state when a vial is installed in the assembly 304. The bellows 330 may expand to accommodate fluid in the event that there is any fluid (e.g., a gas) escaping an installed vial. In other embodiments, the variable volume housing portion 312 may not include a bellows 330. Some embodiments may instead use a flaccid bag-like reservoir instead, for example. In such embodiments, the flaccid reservoir may become more turgid in the event any fluid (e.g., gas) escapes a vial. Also shown in FIG. 9 is a bayonet mount 319 which is included as part of the interface portion 308 of the containment assembly 304.

Figure 10:
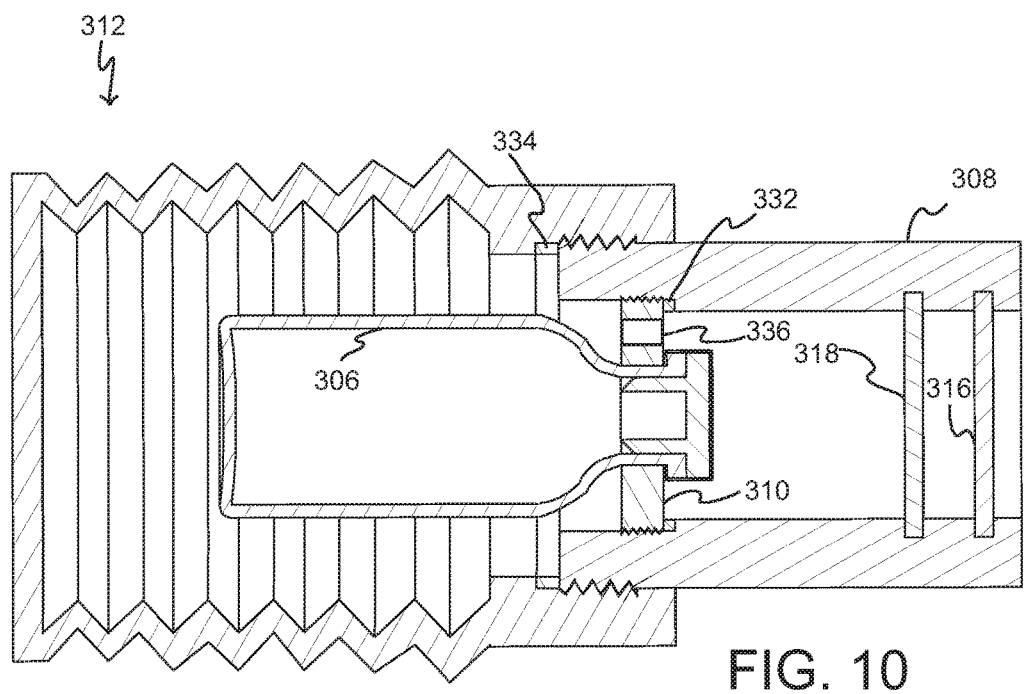
FIG. 10 depicts a cross sectional view taken at a medial and longitudinal plane of the vial containment assembly of FIG. 9.

FIG. 10 depicts a cross sectional view taken at the mid plane of the vial receiving assembly 304 shown in FIG. 9. As shown, a vial 306 is installed in the vial receiving assembly 304. An adapter 310 is in place around the neck of the vial 306. The outer edge of the adapter may be threaded and the interface portion 308 of the vial receiving assembly 304 may thread onto the adapter 310. Once fully threaded onto the adapter 310 a gasket 332 may become compressed between a face of the interface portion 308 and an opposing face of the adapter 310 to create an airtight seal in some embodiments. Other options exist for mating, including but not limited to, a snap fit, sandwich between 308 and 312, etc. In some specific embodiments, there is no gasket 332 or there is the gasket with a pass-through 336).

Similarly, the variable volume housing portion 312 may thread onto a section of the interface portion 308. This threaded engagement may also cause a gasket 334 to become compressed between a face of the variable volume housing 312 and the interface portion 308 creating an airtight seal. The first septum 316 and second septum 318 serve to complete the seal between the interior volume of the vial receiving assembly 304 and the ambient environment.

As shown the adapter 310 may include a pass-through 336 which places the interior volumes of the variable volume housing 312 and interface portion 308 into fluid communication. If any fluid escapes the vial 306, the fluid may pass through the pass-through 336 and into the variable volume housing 312.

Using an embodiment in which fluid may pass through the adapter 310 allow for simplified manufacture of the adapter 310. The adapter 310 may, for example, be made of two pieces of injection mold material which may be snapped, press fit, or otherwise joined together around the neck of the vial 306. In some embodiments the adapter 310 may be airtight or non-airtight.

Though the example embodiment shows the adapter 310 mating with the interface portion 308 and the variable volume housing 312 mating with the interface portion 308, this is not limiting and illustrative. It would be appreciated by one skilled in the art that these sections may mate in any combination so long as the appropriate seals are created and the interior volume of the containment assembly 300 is isolated from the ambient environment. For example, both the interface portion 308 and the variable volume housing 312 may mate with the adapter 310. In some embodiments, the adapter 310 may be an integral part of either the interface portion 308 of the variable volume housing 312. It should also be appreciated that other types of interfaces besides threaded interfaces may be used.

Figure 11:
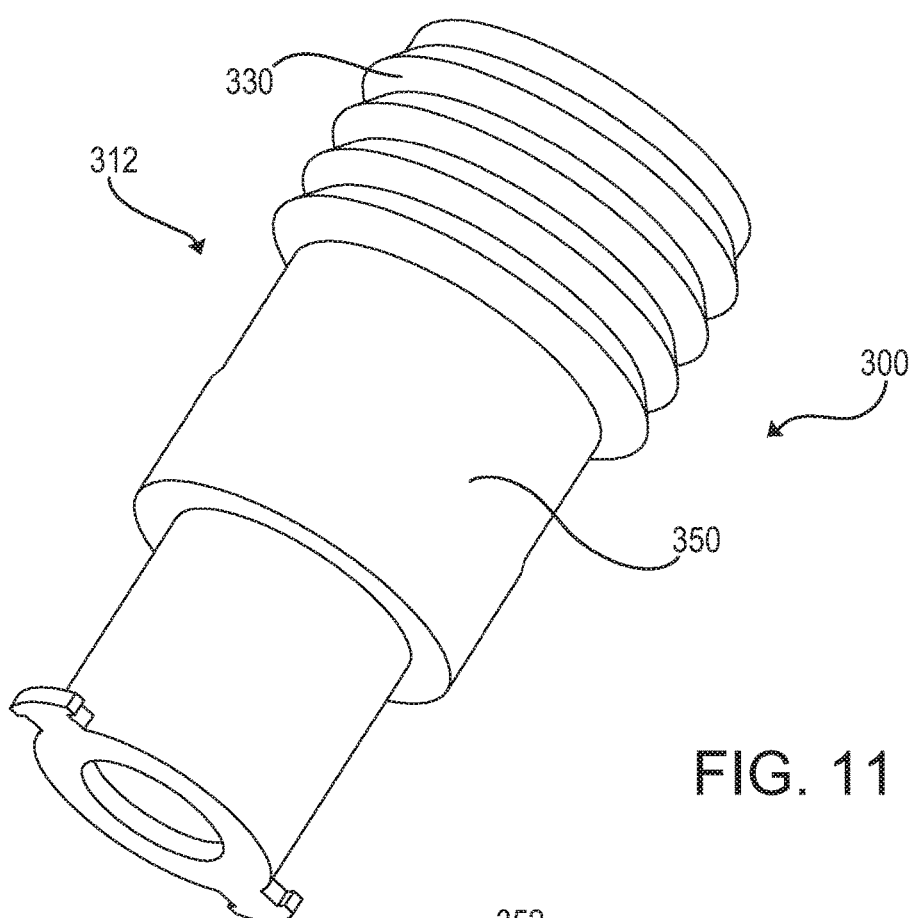
FIG. 11 depicts an example embodiment of a drug reservoir containment assembly.
Figure 12:
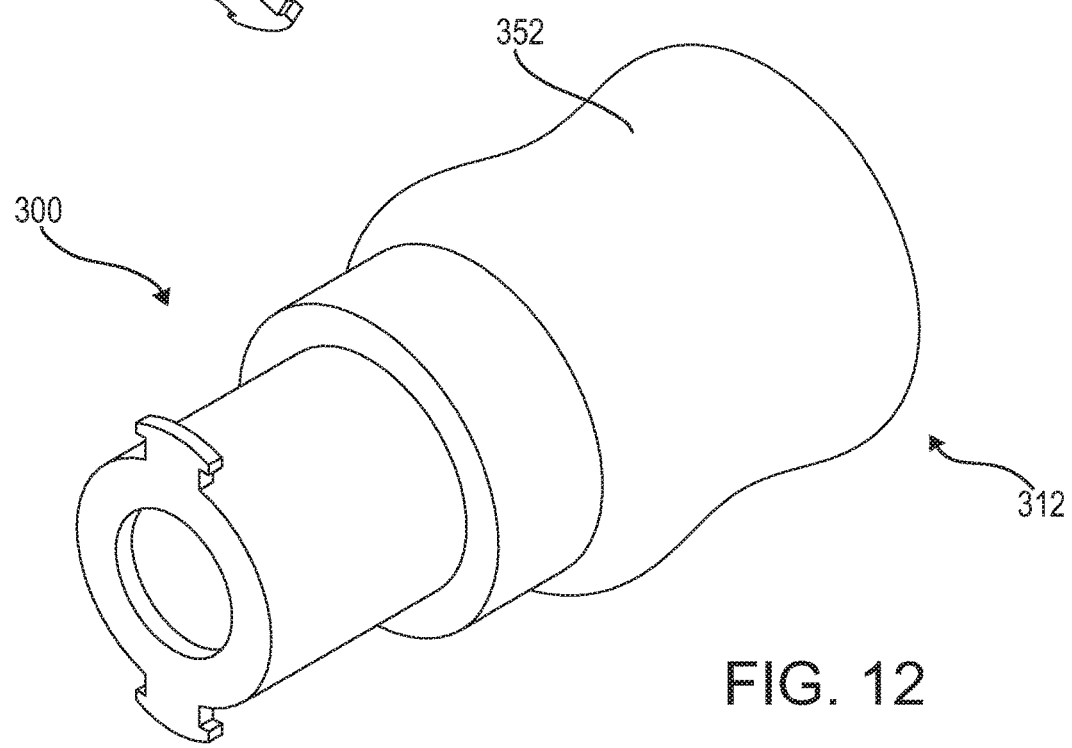
FIG. 12 depicts an example embodiment of a drug reservoir containment assembly.

FIG. 11 and FIG. 12 depict alternate embodiments of a drug reservoir containment assembly 300. The containment assembly 300 shown in FIG. 11 is similar to that shown in FIGS. 9 and 10. The variable volume housing 312 includes a bellows 330 which allows the volume of the variable volume housing 312 to increase in the event that fluid escapes the contained drug reservoir. The variable volume housing 312 in FIG. 11 also includes a window portion 350 in the example embodiment. This window 350 may be transparent and allow a user to view a contained drug reservoir. In the example embodiment, the window 350 is disposed in a position which would allow a user to read the label on a medication vial and view the contents of the vial.

Referring now to FIG. 12, the variable volume housing 312 of the containment assembly 300 is a flaccid elastomeric jacket of bag 352. The elastomeric jacket or bag 352 may be made of a transparent material and obviate the need for a window 350 similar to that shown in FIG. 11. In the event that fluid escapes from a contained medication reservoir, the turgidity of the elastomeric jacket or bag 352 may increase as the fluid is accommodated.

FIGS. 13-15 depict various views of a specific example embodiment of an adapter 310 which may be placed around the neck of a medication vial as a collar. As shown, the adapter 310 may include a first portion 360 and a second portion 362 which may be joined together to surround the neck of a vial. When joined together, an inner void 364 which accommodates the neck of a vial may be formed as shown best in FIG. 15. There may be a number of different adapters 310 each having an inner void 364 of different dimensions in order to accommodate different vials. In such embodiments, it may be desirable that the adapters 310 for different vials may be identical with the exception of the dimensions of the inner void 364. This allows for other components of a containment assembly 300 to be standardized.

In the example embodiment, the first portion 360 and the second portion 362 are identical pieces. It may be desirable that the first portion 360 and second portion 362 of an adapter 310 be identical pieces as it may simplify manufacturing and installation of the adapter 310. Each portion may include a pass through 336 as shown in FIGS. 14 and 15. Each portion may include a mating projection 366 and a receiving structure 368 for a mating projection 366. In the example embodiment, the mating projection 366 and the receiving structure 368 snap fit together. As mentioned above, any coupling scheme which would be known to one skilled in the art may alternatively be used.

Figure 16:
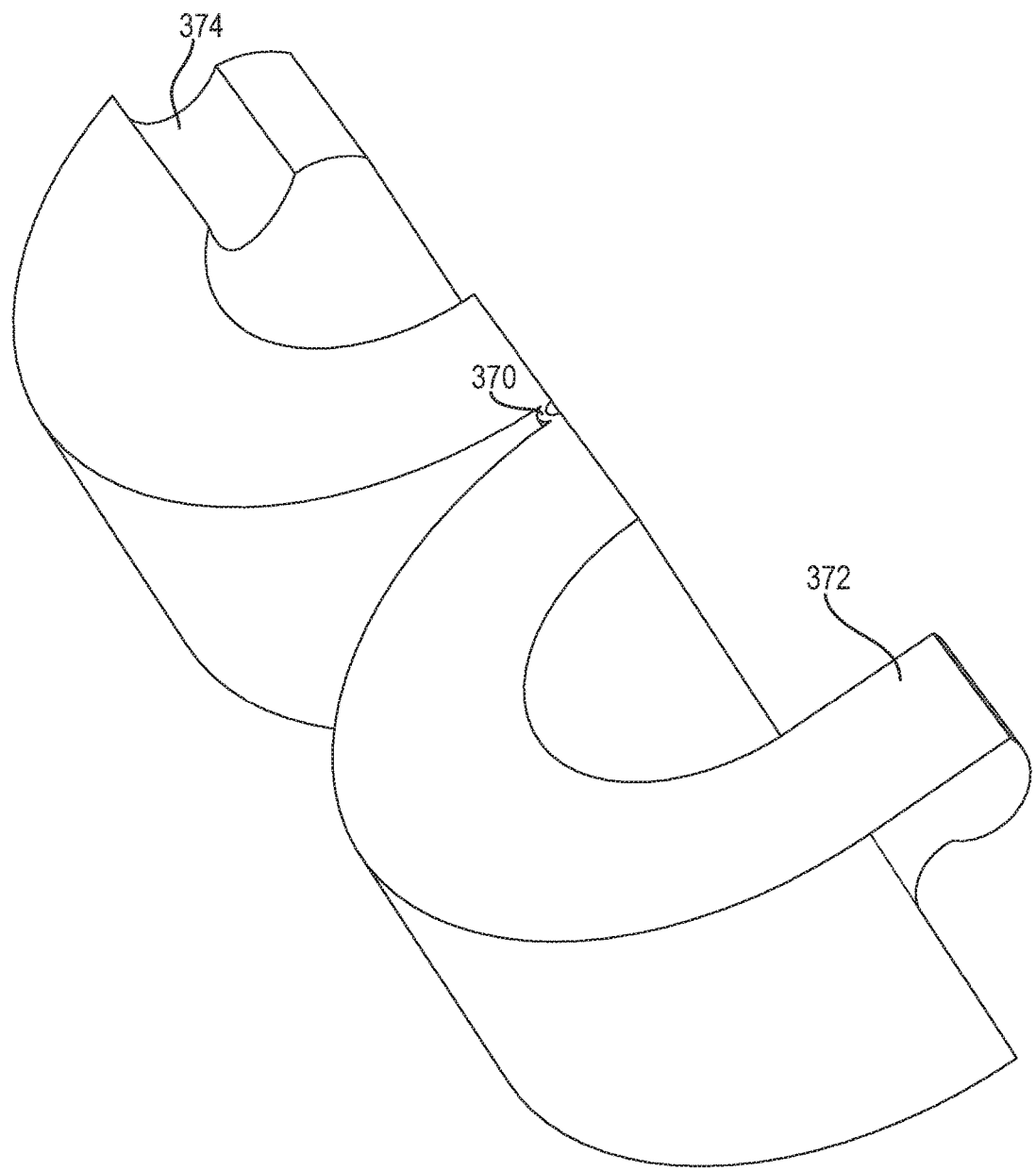
FIG. 16 depicts an example adapter for a drug reservoir containment assembly.

FIG. 16 depicts another specific example embodiment of an adapter 310. As shown, the adapter 310 is a single monolithic piece of material in the example embodiment. The adapter 310 includes a hinge 370 which allow portions of the adapter 310 that flank the hinge 370 to swing closed around the neck of a vial. This hinge 370 may, for example, be a living hinge and be molded as part of the adapter 310 during manufacture. The example adapter 310 includes a projection 372 having a bump feature that may fall into a detent 374 when the adapter 310 is closed around the neck of a vial. When then bump feature of the projection 372 falls into the detent 374, the adapter 310 will effectively lock in place around the neck of a vial.

Figure 17:
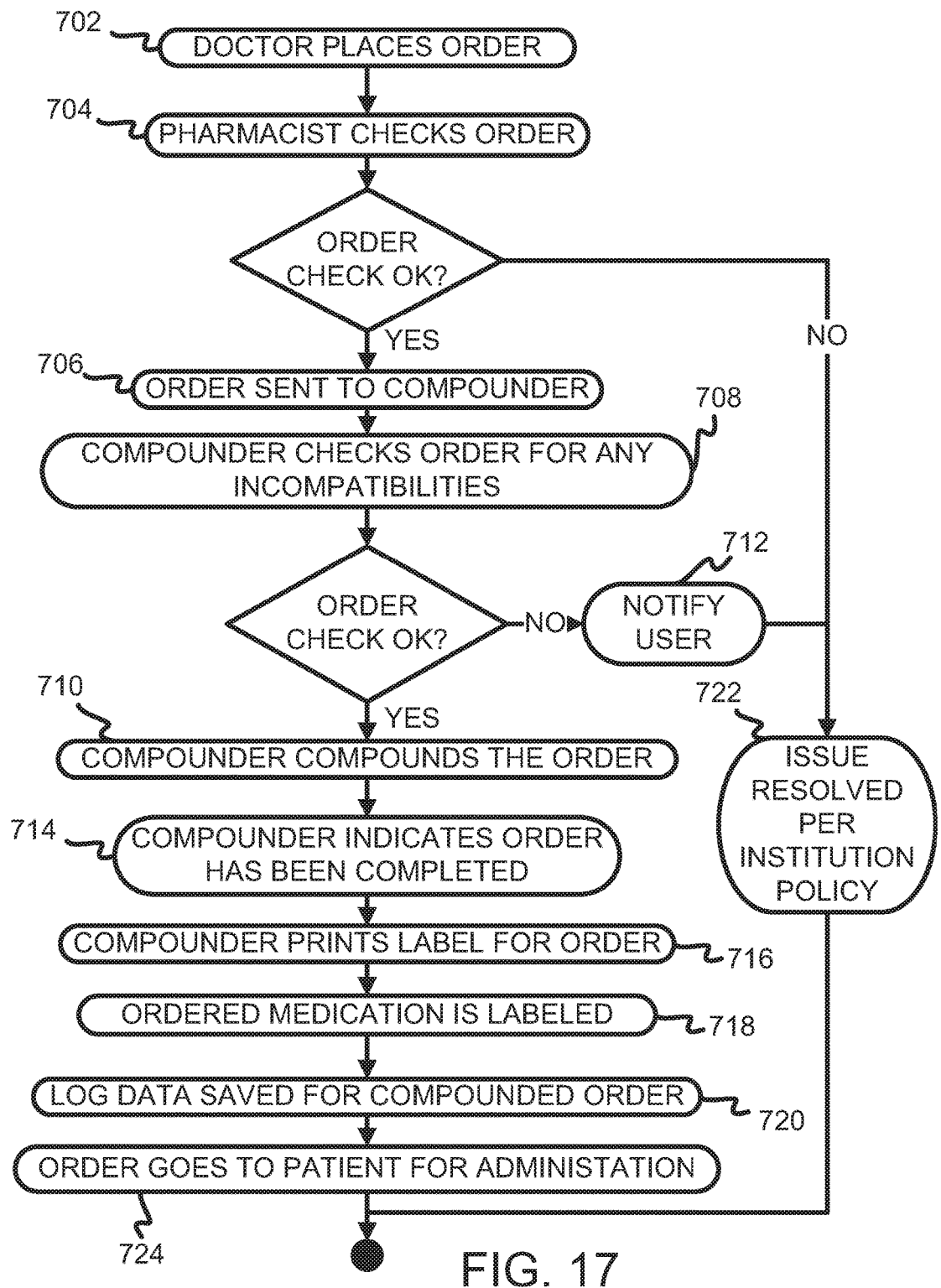
FIG. 17 depicts a flowchart detailing a number of example steps which may be used in creating a desired pharmaceutical compound with a compounder.

FIG. 17 depicts a flowchart detailing a number of example steps which may be used in creating a desired pharmaceutical compound with a compounder. At block 702, a doctor places an order. The doctor may place the order with a computerized physician order entry (CPOE) system. At block 704, a pharmacist may check the order and confirm that the order is correct or that there is an issue with the order. The pharmacy system may also interface with a CPOE system. If the pharmacy order check passes, the order may be sent to the compounder at block 706. At block 706, the order may be sent from a CPOE system to the compounder. If the pharmacy order check fails, the issue may be resolved per institution policy at block 722. The compounder may check the order for incompatibilities at block 708. The compounder may have a drug library file stored in its memory and the compounder may refer to the drug library file to check for drug names, characteristics, contraindications, other incompatibilities, etc. If the compounder order check fails, the user may be notified at block 712. If the user is notified of a failed compounder order check at block 712, the issue may be resolved per institution policy at block 722. If the compounder order check passes, the compounder may compound the order at block 710. After the compounder compounds the order, the compounder may indicate that the order has been completed at block 714. At block 714, the compounder may indicate to other hospital or institutional systems (e.g. CPOE system) that the order has been completed. At block 716, the compounder may print a label for the compounded medication. In some embodiments, the compounder may distribute the compounded order into multiple reservoirs. In such embodiments, the compounder may print multiple labels for the compounded medication. If a label is printed, the compounded medication may be labeled at block 718. At block 720, the log data for the compounder may be saved and/or communicated to other pharmacy or institution systems such as a continuous quality improvement (CQI) system, which may be used for analysis of compounder usage and quality improvement. In some embodiments, a CQI system may interface with the compounder to generate materials for regularly scheduled reviews. The compounded medication may be transported to the patient floor for administration at block 724. In some embodiments, some orders may be stockpiled if the orders lend themselves to such stockpiling (e.g. the orders would not expire in a short time period).

Figure 18:
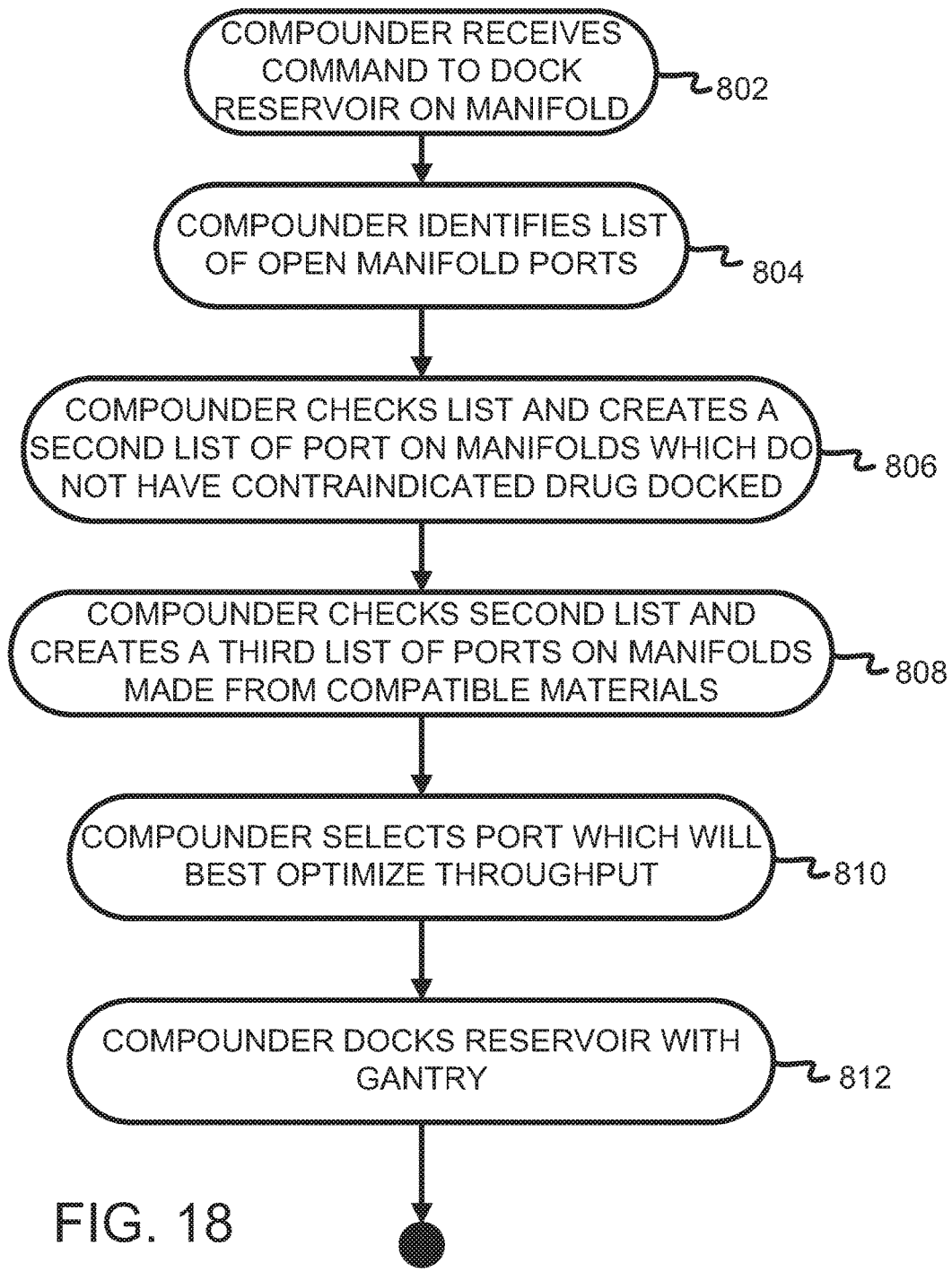
FIG. 18 depicts a flowchart detailing a number of example steps which may be used by a compounder when placing a reservoir on a manifold.

FIG. 18 depicts a flowchart detailing a number of example steps which may be used by a compounder when placing a reservoir on a manifold. At block 802, the compounder may receive a command to dock a reservoir on a manifold. At block 804, the compounder may identify a list of open manifold ports. At block 806, the compounder may check the list of open manifold ports and may create a second list of available manifold ports on manifolds which do not have a related contraindicated drug docked. The compounder may have a drug library file stored in its memory and the compounder may refer to the drug library file to check for contraindications at block 806. At block 808, the compounder may check the second list and may create a third list of ports on manifolds that are made from compatible materials. The compounder may refer to the drug library file to check for compatible materials at block 808. At block 810, the compounder may select a port which will best optimize throughput. For example, the compounder may select a more efficiently located port, such as a port located in close proximity to the current position of a gantry or the like. As another example, the compounder may place commonly combined medications on separate manifolds permitting simultaneous delivery from both manifolds when the medications are being combined. This may be useful to increase throughput of the device. At block 812, the compounder may dock the reservoir to the selected port with the gantry or the like.

Figure 19:
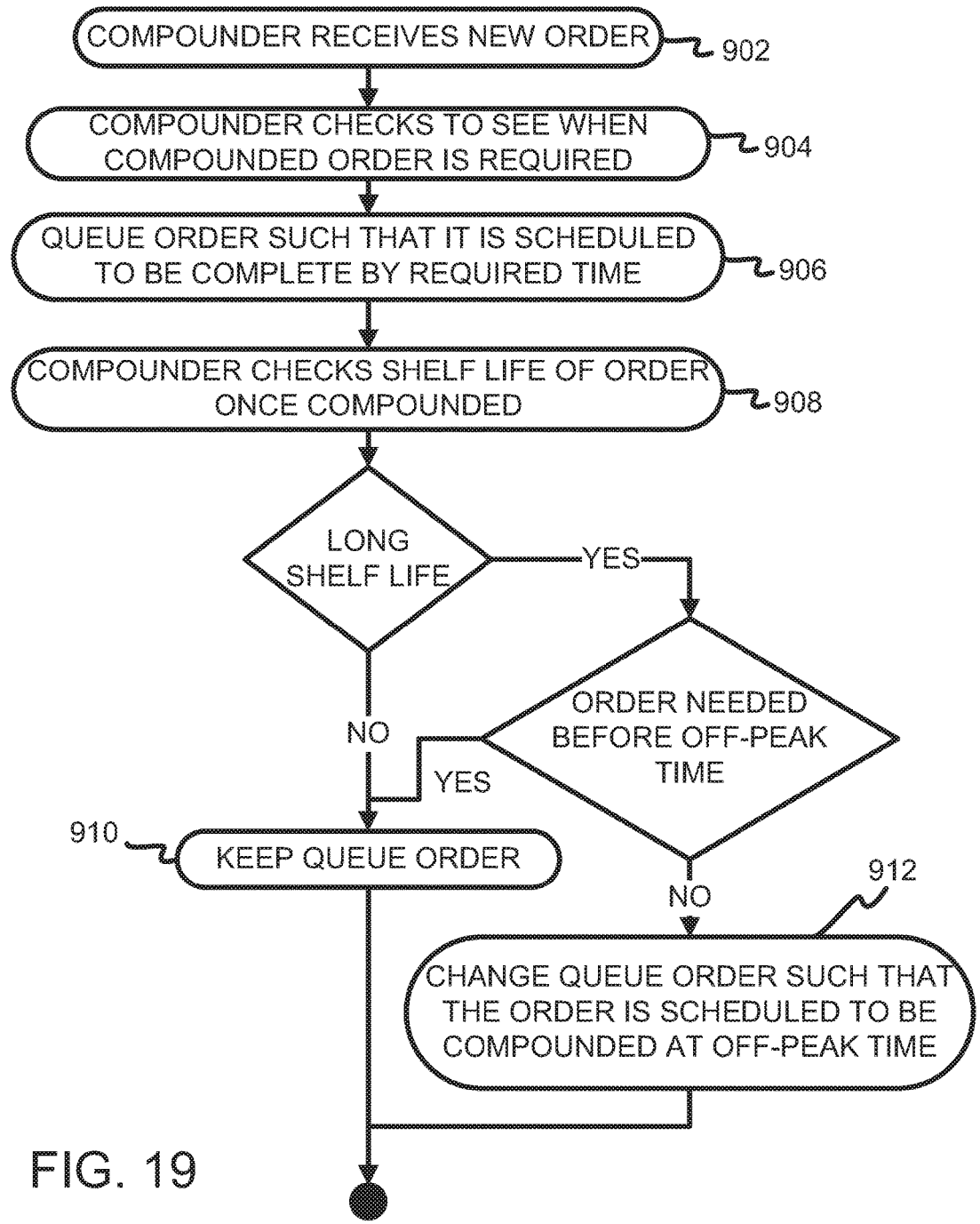
FIG. 19 depicts a flowchart detailing a number of example steps which may be used by a compounder to manage a medication order queue when a new order is received.

FIG. 19 depicts a flowchart detailing a number of example steps which may be used by a compounder to manage a medication order queue when a new order is received. At block 902, the compounder receives a new order. The order may be received by the compounder from a CPOE system. At block 904, the compounder may check to see when the compounded order is required. At block 906, the compounder may queue the order such that it is scheduled to be completed by required time. At block 908, the compounder may check the shelf life of the order once the order is compounded. If the compounded order does not have a long shelf life, the compounder may keep the queue order at block 910. If the compounded order does have a long shelf life but is needed before the soonest off peak time, the compounder may keep the queue order at block 910. An off peak time may be, for example at night (e.g. 1:00 a.m.), when compounding demand is lower. If the compounded order has a long shelf life and is not needed before soonest off peak time, the compounder may change the queue order at block 912 such that the order is scheduled to be compounded at an off peak time.

In various embodiments, a compounder may take other information into consideration when determining a queue location for a new order. In some embodiments, when the compounder is determine where to place a new order in an existing queue, the compounder may search the queue for identical orders or orders for which the same drug cocktail is being compounded. The compounder may then combine these orders and instruct the user to set up multiple destination reservoirs (one or more for each order of the combined orders) when the queue location is reached. In some embodiments, the compounder may queue the order in a manner which would help maximize efficiency of the compounder. For example, the compounder may queue orders such that orders using similar drugs are grouped together to allow the compounder to have a higher throughput. This may be so because it will minimize the number of times manifolds may need to be flushed. By means of example, if five orders all use a particular drug and no other drug on that manifold is needed to produce the order, that compounder may not need to flushed during compounding of those five orders.

Figure 20:
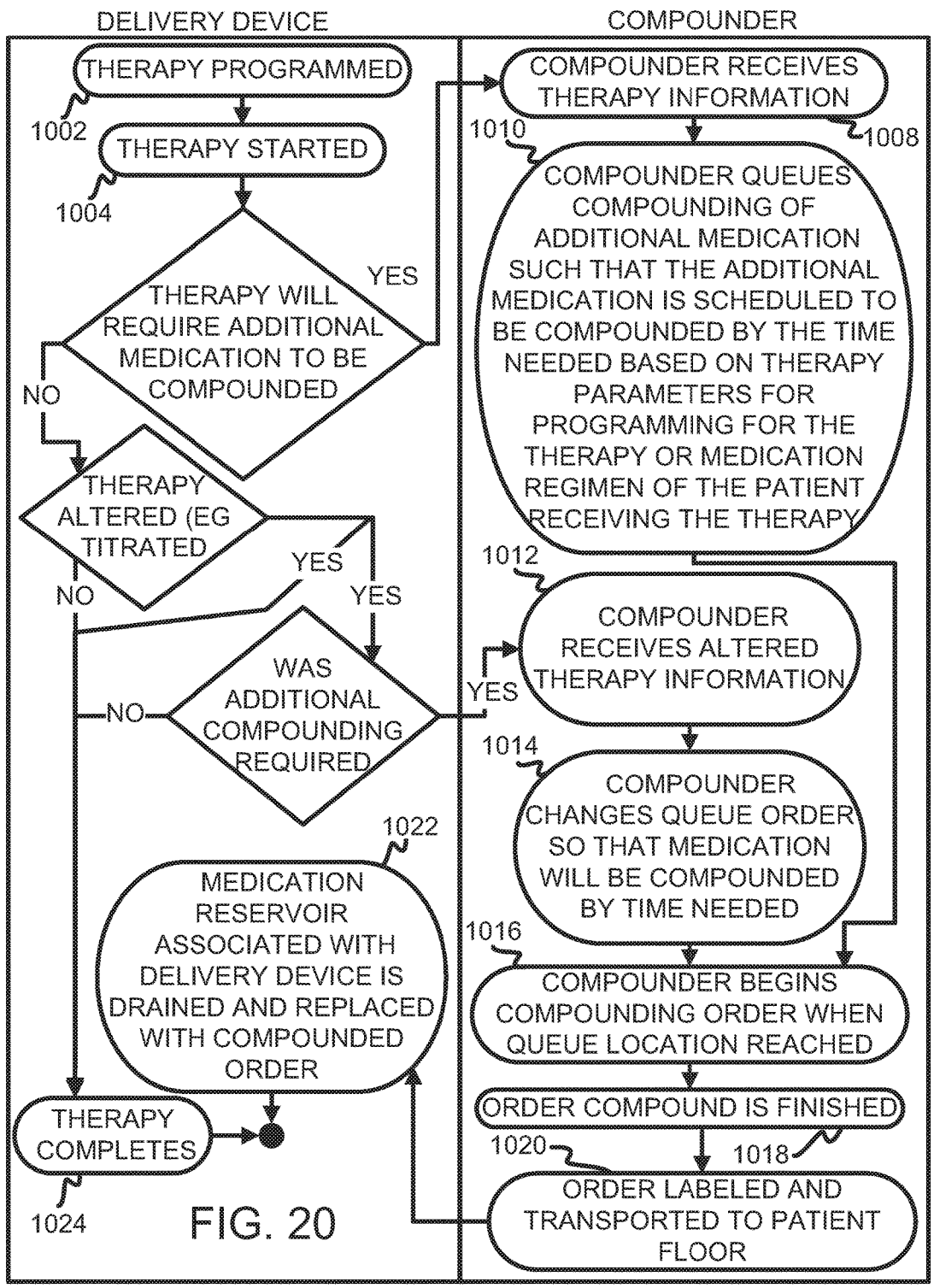
FIG. 20 depicts a flowchart detailing a number of example steps which may be used by a compounder which is included in an integrated system to schedule compounding of drugs.

FIG. 20 depicts a flowchart detailing a number of example steps which may be used by a compounder which is included in an integrated system to schedule compounding of drugs. The flowchart depicted in FIG. 204 assumes that the steps described above in FIG. 17 have been completed and there is compounded medicine available to start the therapy. At block 1002, a therapy is programmed. At block 1004, the therapy is started. If the therapy was not altered (e.g. titrated), the therapy completes at block 1006. If the therapy will require additional medication to be compounded, the compounder may receive therapy information at block 1008. At block 1010, the compounder queues the compounding of the additional medication such that the additional medication is scheduled to be compounded by the time needed based on therapy parameters programmed for the therapy or medication regimen of the patient receiving the therapy. If the therapy is altered (e.g. titrated) after the therapy is started at block 1004 and if additional compounding was required, the compounder may receive altered therapy information at block 1012. At block 1014, the compounder changes the queue order so that medication will be compounded by the time it is needed. After the compounder queues the order in block 1010 or block 1014, the compounder may begin compounding the order at block 1016 when the queue location is reached. At block 1018, the order compounding is finished. At block 1020, the order is labeled and transported to the patient floor. At block 1022, the medication reservoir associated with the delivery device is drained and replaced with the compounded order. During one therapy, the above described cycle may be repeated once or several times if the therapy requires additional medication to be compounded. If further compounding is required, the compounder may receive therapy information at block 1008 and repeat the discussed cycle through block 1022. When no further compounding is required, the therapy completes at block 1006. Alternatively, the example steps above may be utilized to meet the needs of a medication regimen rather than an individual therapy. The medication regimen may be defined in another hospital or institution system which interfaces with the compounder (e.g. an auto-programming system, patient medical record system, auto-refill order system, CPOE system, etc.).

Figure 21:
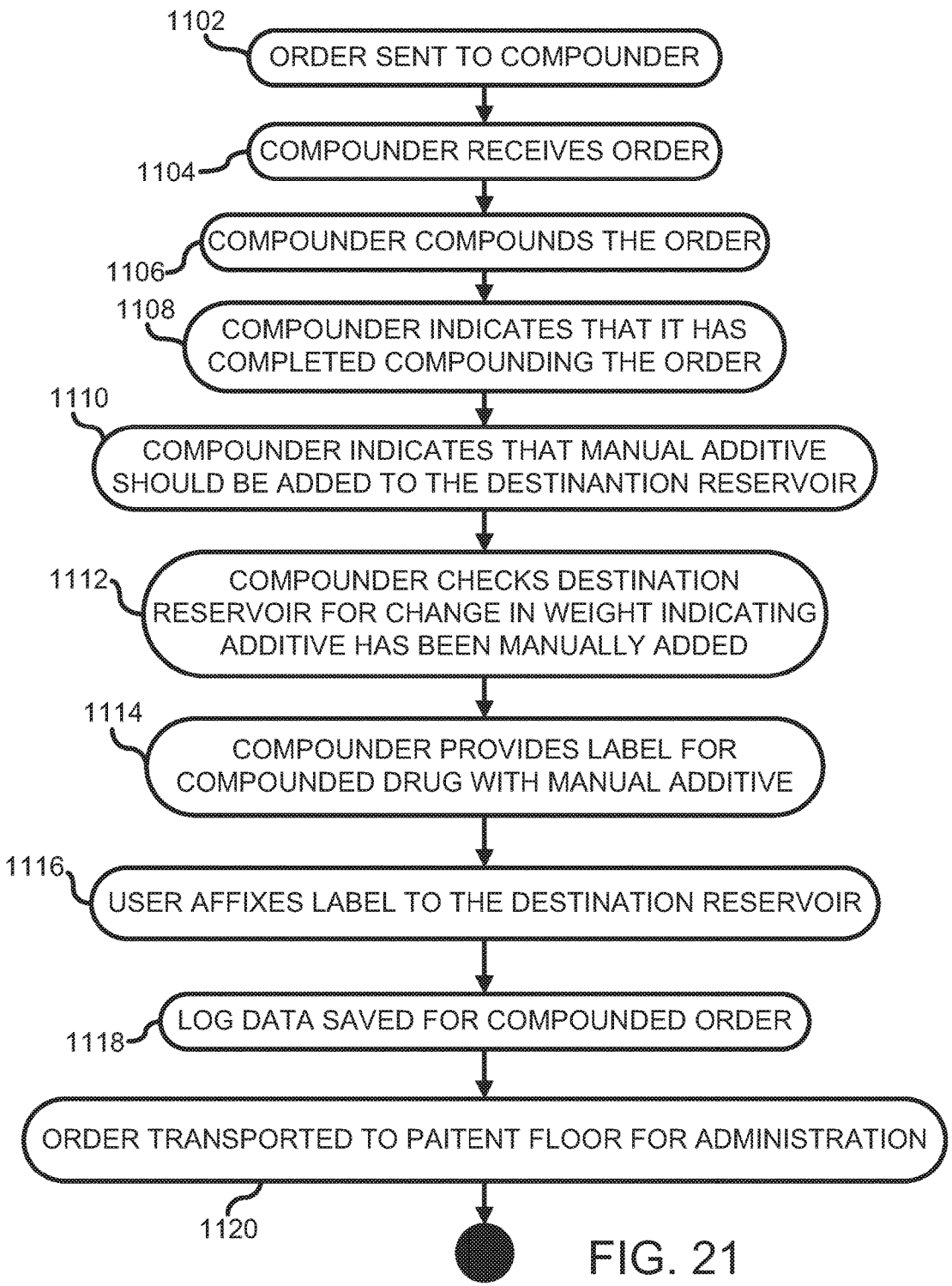
FIG. 21 depicts a flowchart detailing a number of example steps which may be used in creating, with a compounder, a desired pharmaceutical compound having a manual additive.

FIG. 21 depicts a flowchart detailing a number of example steps which may be used in creating, with a compounder, a desired pharmaceutical compound having a manual additive. At block 1102, an order is sent to a compounder. At block 1104, the compounder receives the order. The order may be received by the compounder from a CPOE system. At block 1106, the compounder compounds the order. At block 1108, the compounder may indicate that is has completed compounding the order. The compounder may communicate to other hospital or institution system, such as a CPOE system, that the compounder has completed compounding the order. At block 1110, the compounder may indicate that manual additive should be added to the destination reservoir. In some embodiments, a user may specify the name of the additive or one or more characteristics of the additive (e.g. specific gravity). At block 1112, the compounder checks the destination reservoir for a change in weight indicating that additive has been manually added. The compounder may check the destination reservoir for a change in weight by utilizing a load cell such as load cell 126 shown in FIG. 6. At block 1114, the compounder may provide labels as needed for the compounded drug with manual additive. At block 1116, the user may affix the label(s) to the destination reservoir(s). At block 1118, the log data for the compounded order may be saved. At block 1120, the order may be transported to the patient floor for administration.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g. "a" "an" or "the", this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B. This expression signifies that, with respect to the present disclosure, the only relevant components of the device are A and B.

Furthermore, the terms "first", "second", "third" and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

What is claimed is:

1. A containment assembly for enclosing a medication container, the containment assembly comprising:
   an interface portion having a proximal end and a distal end, the interface portion including a housing wall which defines a channel spanning from the proximal end to the distal end;
   at least one pierceable septum disposed at least at one of:
      on the proximal end of the channel, and
      within the channel forming a barrier between the proximal end of the channel and the distal end of the channel;
   a variable-volume housing portion having a variable volume chamber, the variable-volume chamber of the variable-volume housing portion being in fluid communication with the distal end of the channel, wherein the distal end of the interface portion includes a mating feature which mates with a cooperating mating feature of the variable-volume housing portion; and
   a gasket member configured to compress between the interface portion and the variable-volume housing portion when the interface portion is mated to the variable-volume housing portion.

2. A containment assembly for enclosing a medication container, the containment assembly comprising:
   an interface portion having a proximal end and a distal end, the interface portion including a housing wall which defines a channel spanning from the proximal end to the distal end;
   at least one pierceable septum disposed at least at one of:
      on the proximal end of the channel, and
      within the channel forming a barrier between the proximal end of the channel and the distal end of the channel; and
   a variable-volume housing portion having a variable volume chamber, the variable-volume chamber of the variable-volume housing portion being in fluid communication with the distal end of the channel; and
   an adapter member having a mating feature configured to mate with a cooperating mating feature on one of the interface portion and the variable-volume housing portion.

3. The containment assembly of claim 2, wherein the adapter member is a collar which is adapted to fit around a portion of the medication container.

4. The containment assembly of claim 2, wherein the adapter member is a collar which is adapted to fit around a neck of the medication container.

5. The containment assembly of claim 2, wherein the adapter member includes at least one pass-through allowing for fluid communication between the distal end of the channel and the variable-volume chamber.

6. A containment assembly for enclosing a medication container, the containment assembly comprising:
   an interface portion having a proximal end and a distal end, the interface portion including a housing wall which defines a channel spanning from the proximal end to the distal end;
   at least one pierceable septum disposed at least at one of:
      on the proximal end of the channel, and
      within the channel forming a barrier between the proximal end of the channel and the distal end of the channel; and
   a variable-volume housing portion having a variable volume chamber, the variable-volume chamber of the variable-volume housing portion being in fluid communication with the distal end of the channel; and
   at least two pierceable septa of the at least one pierceable septum disposed within the channel, a first septum of the at least two pierceable septa disposed proximal the proximal end, a second septum of the at least two pierceable septa disposed distal to the proximal end relative to the first septum.

7. The containment assembly as in any one of claims 2 and 6, wherein the distal end of the interface portion includes a mating feature which mates with a cooperating mating feature of the variable-volume housing portion.

8. The containment assembly of claim 7, further comprising a gasket member configured to compress between the interface portion and the variable-volume housing portion when the interface portion is mated to the variable-volume housing portion.

9. The containment assembly as in any one of claims 1, 2, and 6, wherein the variable-volume chamber is formed from an elastomeric material.

10. The containment assembly as in any one of claims 1, 2, and 6, wherein the variable-volume chamber includes at least one expandable feature.

11. The containment assembly of claim 10, wherein the at least one expandable feature is a collapsible pleat.

12. The containment assembly as in any one of claims 1, 2, and 6, wherein the variable-volume housing portion includes a window.

13. A containment assembly for enclosing a medication container, the containment assembly comprising:
   an interface portion having a proximal end and a distal end, the interface portion including a housing wall which defines a channel spanning from the proximal end to the distal end;
   a plurality of elastomeric septa disposed within the channel forming a barrier between the proximal end of the channel and the distal end of the channel; and
   a variable-volume housing portion, at least a portion of the variable-volume housing portion being a variable volume formed of an elastomeric material.

14. The containment assembly of claim 13, wherein the variable-volume of the variable-volume housing portion is in fluid communication with the distal end of the channel.

15. The containment assembly of claim 13, wherein the variable-volume housing portion includes a pressure port configured for connection to a pressure source.

16. The containment assembly of claim 15, wherein the pressure port is a vacuum port and the pressure source is a vacuum source.

17. The containment assembly of claim 13, wherein the variable volume is a flaccid enclosure.

18. The containment assembly of claim 13, further comprising a collar member which couples with one of the interface portion or the variable-volume housing portion, the collar member sized to fit around a neck of the medication container.

19. The containment assembly of claim 18, wherein the collar member includes a passage which allows for fluid communication between the distal end of the channel and the variable volume.

20. The containment assembly of claim 18, wherein the collar member comprises a first part and a second part, the first and second parts having cooperating coupling features which engage to couple the first part and the second part together.

* * * * *